United States Patent
Pohlmann et al.

(10) Patent No.: US 9,511,064 B2
(45) Date of Patent: Dec. 6, 2016

(54) COMBINATION THERAPY FOR THE TREATMENT OF CANCER AND IMMUNOSUPPRESSION

(71) Applicants: Basilea Pharmaceutica AG, Basel (CH); Universität Basel, Basel (CH)

(72) Inventors: Jens Pohlmann, Basel (CH); Don Gary Benjamin, Basel (CH); Christoph Moroni, Biel-Benken (CH)

(73) Assignee: BASILEA PHARMACEUTICA AG, Bassel (CH)

( * ) Notice: Subject to any disclaimer, the term of this patent is extended or adjusted under 35 U.S.C. 154(b) by 0 days.

(21) Appl. No.: 14/413,122

(22) PCT Filed: Jul. 3, 2013

(86) PCT No.: PCT/EP2013/064048
§ 371 (c)(1),
(2) Date: Jan. 6, 2015

(87) PCT Pub. No.: WO2014/009222
PCT Pub. Date: Jan. 16, 2014

(65) Prior Publication Data
US 2015/0157622 A1 Jun. 11, 2015

(30) Foreign Application Priority Data
Jul. 10, 2012 (EP) .................................... 12175724

(51) Int. Cl.
| | |
|---|---|
| C07D 221/18 | (2006.01) |
| A61K 31/475 | (2006.01) |
| C07D 459/00 | (2006.01) |
| A61K 31/155 | (2006.01) |
| A61K 31/365 | (2006.01) |
| A61K 45/06 | (2006.01) |
| C07D 471/14 | (2006.01) |
| G01N 33/50 | (2006.01) |

(52) U.S. Cl.
CPC ........... *A61K 31/475* (2013.01); *A61K 31/155* (2013.01); *A61K 31/365* (2013.01); *A61K 45/06* (2013.01); *C07D 459/00* (2013.01); *C07D 471/14* (2013.01); *G01N 33/5011* (2013.01); *G01N 2458/00* (2013.01); *G01N 2500/10* (2013.01)

(58) Field of Classification Search
None
See application file for complete search history.

(56) References Cited

U.S. PATENT DOCUMENTS 2,813,871 A * 11/1957 Lucas .................. C07D 459/00
546/54
8,993,587 B2 * 3/2015 Benjamin .............. A61K 45/06
514/280
2010/0239522 A1 9/2010 Salsbury, Jr. et al.

FOREIGN PATENT DOCUMENTS

WO 2012095379 7/2012
WO WO 2012095379 A1 * 7/2012

OTHER PUBLICATIONS

Hinke, SA et al., Brit. J. Pharmacol. 2007, vol. 150, pp. 1031-1043.*
Silverman, R. The Organic Chemistry of Drug Design and Drug Action 2004, NY Elsevier, p. 26.*
The International Search Report and Written Opinion, mailed on Aug. 7, 2013, in the related PCT Appl. No. PCT/EP2013/064048.
R. A. Lucas, et al., "Rauwolfia Alkaloids. XXXI. The Synthesis and Activity of Some Reserpine Analogs," J. Am. Chem. Soc., 1959, 81 (8), pp. 1928-1932.

* cited by examiner

Primary Examiner — Heidi Reese

(57) ABSTRACT

The invention relates to novel Rauwolfia alkaloid derivatives of formula (I) combinations of Rauwolfia alkaloid derivatives and a mitochondrial inhibitor, e.g. metformin, and the use of Rauwolfia alkaloid derivatives in combination with mitochondrial inhibitor for the treatment of cancer and for achieving clinical immunosuppression. The invention also relates to a fluorescence-based method for predicting the sensitivity of a cancer cell towards a compound of formula (I).

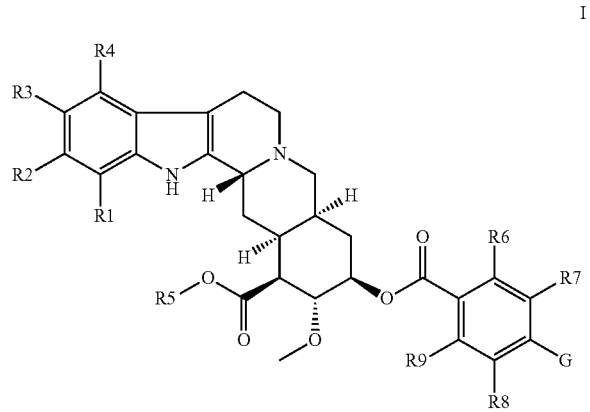

25 Claims, No Drawings

COMBINATION THERAPY FOR THE TREATMENT OF CANCER AND IMMUNOSUPPRESSION

This application is a National Stage Application of PCT/EP2013/064048 filed Jul. 3, 2013, which claims priority from European Patent Application No. 12175724.9, filed on Jul. 10, 2012. The priority of both said PCT and European Patent Application are claimed. Each of the prior mentioned applications is hereby incorporated by reference herein in its entirety.

The invention relates to combinations of Rauwolfia alkaloid derivatives and a mitochondrial inhibitor, novel Rauwolfia alkaloid derivatives of formula (I) and the use of said combinations of Rauwolfia alkaloid derivatives and mitochondrial inhibitors for the treatment of cancer and for achieving clinical immunosuppression.

Anti-cancer therapy utilizes a combination of therapeutic interventions such as surgery, radiation therapy and chemotherapy. Surgery and radiation therapy are generally confined locally to the main site of tumor growth, while chemotherapy is applied to prevent tumor re-growth or against distant tumor foci. Chemotherapeutic agents are also used to reduce tumor growth to manage disease progression when radiotherapy or surgery is not an option.

Immunosuppressive agents are clinically used to suppress a pathological immune reaction which targets the own body (autoimmunity) or overshooting immune reactions as seen in allergy. They are also used to treat transplant rejection caused by the immune system. Basic to immune responses is activation and proliferation of T cells following antigenic stimulation, which act in turn as helper cells for B cells, regulatory cells or effector cells. Immunosuppressive agents such as rapamycin or cyclosporine A act by inhibiting early T cell activation/proliferation. As both cancer and immune responses involve cell proliferation, some agents, for example rapamycin or its analogs, were initially used for immunosuppression but found later application as anticancer agents (Recher et al., Blood 2005, 105:2527-34).

Chemotherapeutic drugs are most effectively used in combination therapy. The rationale is to apply drugs that work via different mechanisms in order to decrease the probability of developing drug-resistant cancer cells. Combination therapy also allows, for certain drug combinations, an optimal combined dose to minimize side effects. This is crucial as standard chemotherapeutic agents target essential cellular process such as DNA replication, cell division or induce DNA damage and thus have a general cytotoxic effect. Finally, combination treatment of two compounds may uncover unanticipated synergisms and trigger effects not induced by a single compound. In recent years, drugs are also used in a neoadjuvant setting, i.e. prior to surgery, to reduce the tumor mass or to improve long-term survival.

The Rauwolfia alkaloid derivatives of formula (I) are synthetic derivatives of reserpine, an anti-hypertensive and anti-psychotic agent (J.A.M.A., Vol. 170, Nr. 17, Aug. 22, 1959, p. 2092). Reserpine and its derivatives like syrosingopine are rarely used today due to the development of better drugs with fewer side-effects. Reserpine acts by inhibition of the vesicular monoamine transporter leading to catecholamine depletion and this mode of action is believed to be shared by all the reserpine derivatives with an anti-hypertensive effect.

Mitochondria contain the energy generating system of a cell, whereby electrons from metabolism pass through complexes I-IV of the electron transfer chain (ETC) leading to extrusion of protons from complex I, III and IV and to a reflux of protons through complex V with concomitant formation of chemical energy in the form of adenosine triphosphate (ATP). Oxygen serves as the ultimate electron acceptor and is reduced to $H_2O$. Critical in this process is the inner mitochondrial membrane, as protons extruded from the complexes pass from the matrix through this membrane into the inter-membrane space, generating a positive membrane potential of 150-200 mV. Dyes such as TMRM (tetramethylrhodamine methyl ester) pass this membrane and accumulate in the mitochondrial matrix, whereby the intensity of the fluorescent signal depends on the strength of the membrane potential. A number of well described agents inhibit mitochondrial function and may be regarded as mitochondriotoxic agents. So called uncoupling agents such as FCCP (carbonyl cyanide-p-trifluoromethoxyphenylhydrazone) uncouple the flow of protons from ATP synthesis, leading to a collapse of the membrane potential with resulting loss of ATP synthesis. A number of well described mitochondrial inhibitors target the different complexes of the ETC including metformin, rotenone, epiberberine, piericidin A (all inhibitors of complex I), sodium malonate and thenoyltrifluoroacetone (inhibitors of complex II), antimycin A (complex III inhibitor), potassium cyanide and sodium azide (inhibitors of complex IV), and oligomycin (complex V inhibitor). Mitochondria are believed to be ancestrally engulfed bacteria. They contain a DNA genome encoding several components of the ETC, as well as components of the mitochondrial ribosome. Agents targeting the mitochondrial genome such as certain HIV-inhibitors of the class of nucleoside analogs, e.g. stavudine (D4T), are toxic for mitochondria as they ultimately destroy the ETC and the mitochondrial energy generating system.

Metformin is a widely used biguanide drug for type 2 diabetes. It is related to buformin and phenformin, two biguanides not used anymore in diabetes therapy due to toxicity. The main clinical benefit of metformin in the treatment of type 2 diabetes is the suppression of hepatic gluconeogenesis to reduce hyperglycemia and improved insulin sensitivity; these effects are believed to be exerted by metformin-dependent stimulation of AMP-activated protein kinase (AMPK) activity. Basic to this effect is the fact, that metformin and other biguanides inhibit complex I of the respiratory chain (electron transfer chain) of mitochondria (El-Mir et al., J Biol Chem 2000, 275:223-228). A meta-analysis of diabetic patients receiving metformin versus an unrelated anti-diabetic agent revealed that the metformin receiving cohort had lower incidence of cancer (Evans et al., BMJ 2005, 330:1304-5; Bowker et al., Diabetes Care 2006, 29:254-8). This has stimulated recent research into the use of metformin as an anti-cancer agent or prophylactic with numerous studies and trials in progress, see Gonzalez-Angulo et al., Clin Cancer Res 2010, 16:1695-700.

It has now been found that Rauwolfia alkaloid derivatives of formula (I) described hereinbelow are useful in the treatment of cancer or autoimmune diseases or in an immunosuppressive treatment when used in combination with mitochondrial inhibitors.

In its broadest aspect the present invention therefore relates to a compound of formula (I):

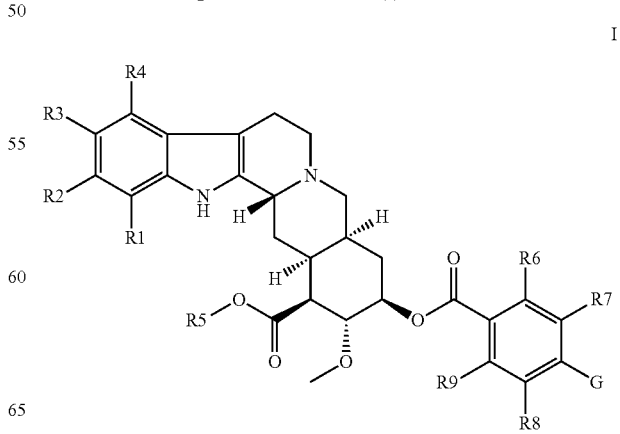

with the exception of syrosingopine, wherein:
R1, R3 and R4 independently of one another represent: hydrogen, $C_1$-$C_3$ alkyl, halogen, $C_1$-$C_3$ alkoxy, amino, $C_1$-$C_3$ alkylamino, $C_1$-$C_3$ dialkylamino, or hydroxyl;
R2 represents hydrogen, $C_1$-$C_3$ alkyl, halogen, amino, $C_1$-$C_3$ alkylamino, $C_1$-$C_3$ dialkylamino, or a group —OR2a;
R2a represents hydrogen, $C_1$-$C_3$ alkyl, formyl or an optionally substituted group selected from alkylcarbonyl, alkoxycarbonyl, arylcarbonyl and heteroarylcarbonyl;
R5 represents $C_1$-$C_4$ alkyl
R6, R7, R8 and R9 independently of one another represent: hydrogen, $C_1$-$C_3$ alkyl, halogen, $C_1$-$C_3$ alkoxy, amino, $C_1$-$C_3$ alkylamino, $C_1$-$C_3$ dialkylamino or hydroxyl;
G represents a group selected from:
—OCO$_2$(CH$_2$)$_n$-A1, —OC(=O)CH$_2$-A2, —CH$_2$OC(=O)-A2, —CH$_2$OCO$_2$-A2, —CH$_2$NHCO$_2$-A2 and —CH$_2$CO$_2$-A2, wherein
A1 represents an optionally substituted group selected from alkyl, aryl, heteroaryl, cycloalkyl and heterocyclyl,
A2 represents an optionally substituted group selected from alkyl, cycloalkyl, heterocyclyl, —(CH$_2$)$_n$-aryl and —(CH$_2$)$_n$-heteroaryl and
n represents 0, 1, 2 or 3,
for use in the treatment of cancer or autoimmune diseases or in an immunosuppressive treatment in combination with a mitochondrial inhibitor and furthermore to a mitochondrial inhibitor for use in the treatment of cancer or autoimmune diseases or in an immunosuppressive treatment in combination with a compound of said formula (I).

Some compounds of formula (I) are already known, in particular certain compounds of said formula, wherein R2 is hydrogen or methoxy and A1 is alkyl.

In another aspect, the invention therefore also relates to compounds of the above formula (I), wherein
R1, R3 and R4 independently of one another represent: hydrogen, $C_1$-$C_3$ alkyl, halogen, $C_1$-$C_3$ alkoxy, amino, $C_1$-$C_3$ alkylamino, $C_1$-$C_3$ dialkylamino, or hydroxyl;
R2 represents hydrogen, $C_1$-$C_3$ alkyl, halogen, amino, $C_1$-$C_3$ alkylamino, $C_1$-$C_3$ dialkylamino, or a group —OR2a;
R2a represents hydrogen, $C_1$-$C_3$ alkyl, formyl or an optionally substituted group selected from alkylcarbonyl, alkoxycarbonyl, arylcarbonyl and heteroarylcarbonyl;
R5 represents $C_1$-$C_4$ alkyl
R6, R7, R8 and R9 independently of one another represent: hydrogen, $C_1$-$C_3$ alkyl, halogen, $C_1$-$C_3$ alkoxy, amino, $C_1$-$C_3$ alkylamino, $C_1$-$C_3$ dialkylamino or hydroxyl;
G represents a group selected from:
—OCO$_2$(CH$_2$)$_n$-A1, —OC(=O)CH$_2$-A2, —CH$_2$OC(=O)-A2, —CH$_2$OCO$_2$-A2, —CH$_2$NHCO$_2$-A2 and —CH$_2$CO$_2$-A2, wherein
A1 represents an optionally substituted group selected from alkyl, aryl, heteroaryl, cycloalkyl and heterocyclyl,
A2 represents an optionally substituted group selected from alkyl, cycloalkyl, heterocyclyl, —(CH$_2$)$_n$-aryl and —(CH$_2$)$_n$-heteroaryl and
n represents 0, 1, 2 or 3,
with the proviso that R2 in formula (I) must not be hydrogen or methoxy when A1 is an alkyl group.

Where not defined differently herein, the term "alkyl" as used in this application includes in particular optionally substituted branched or unbranched alkyl groups having e.g. 1 to 10 carbon atoms, preferably $C_1$-$C_6$alkyl, more preferably $C_1$-$C_4$alkyl, including e.g. methyl, ethyl, propyl (n-propyl or isopropyl), butyl (n-butyl, isobutyl or tertiary-butyl), pentyl (including n-pentyl and isopentyl) or branched and unbranched hexyl, heptyl or octyl residues. $C_1$-$C_3$alkyl is most preferred, in particular methyl and ethyl.

The term "cycloalkyl" as used herein refers preferably to optionally substituted cycloalkyl groups having 3 to 12 ring atoms which may be arranged in one or more rings, more preferably to $C_3$-$C_{10}$cycloalkyl like e.g. $C_3$-$C_7$cycloalkyl. Preferred specific examples of cycloalkyl moieties include optionally substituted cyclopropyl, cyclobutyl, cyclopentyl, cyclohexyl or cycloheptyl groups.

For the purposes of the present invention, the term "heterocyclyl" refers to non-aromatic ring systems having 3 to 10 ring atoms which may be arranged in one or more rings, wherein one, two, three or four of the carbon ring atoms are replaced by a heteroatom selected from heteroatoms such as N, O or S. Monocyclic $C_3$-$C_7$heterocyclyl groups are particularly preferred, including, but not limited to morpholyl, thiomorpholyl, piperazyl, piperidyl, tetrahydrofuryl, pyrrolidyl, oxazolyl, 1H-pyrazolyl, 1H-tetrazolyl and the like. The heterocycloalkyl groups are optionally substituted as described below. They can also include one or more unsaturated bond, in particular doublebond like e.g. 2H-pyrrol, 4H-imidazol, 4-H-pyrazol, 4H-oxazol or 4H-isooxazol or 2H- or 4H-pyran.

As used herein, the term "aryl" means a carbocyclic aromatic group having 6 to 14, preferably 6 to 10 ring atoms. Examples of aryl groups are phenyl, naphthyl and the like. A particularly preferred example of aryl is phenyl. The aryl group described above may be substituted independently with one, two, or three substituents, preferably one or two substituents as described below.

The term "heteroaryl" means a monocyclic or bicyclic radical of 5 to 14, preferably 5 to 10, more preferably 5 or 6, ring atoms with at least one aromatic ring containing one, two, or three ring heteroatoms selected from N, O, and S, the remaining ring atoms being C. One or two ring carbon atoms of the heteroaryl group may optionally be replaced with a carbonyl group. Preferred examples of heteroaryl are pyridyl, pyrazinyl, pyrimidyl, thiophenyl, oxadiazolyl, pyrazolyl, oxazolyl, triazolyl, tetrazolyl, 1,8-naphthyridinyl, quinoxalinyl, quinazolinyl, indolizinyl, phenantridinyl, phenothiazinyl or phenoxazinyl and the like. The heteroaryl group described above may optionally be substituted with one, two, or three substituents, preferably one or two substituents as described below.

Preferred optional substituents of the aforementioned alkyl, cycloalkyl, heterocyclyl, aryl or heteroaryl groups include halogen, in particular fluoro, chloro, bromo and iodo, hydroxyl, alkoxy, in particular $C_1$-$C_3$ alkoxy, amino, $C_1$-$C_3$ alkylamino, $C_1$-$C_3$ dialkylamino, cyano and carboxy and the like. Other preferred substituents include alkyl substituents, in particular $C_1$-$C_3$alkyl, and haloalkyl substituents, in particular halo $C_1$-$C_3$alkyl substituents, like e.g. trifluoromethyl.

Particularly preferred compounds of formula (I) are on one hand the compounds wherein G represents a group selected from:
—OCO$_2$(CH$_2$)$_n$-A1, —OC(=O)CH$_2$-A2, —CH$_2$OC(=O)-A2, —CH$_2$OCO$_2$-A2, —CH$_2$NHCO$_2$-A2 and —CH$_2$CO$_2$-A2, wherein
A1 represents an optionally substituted group selected from aryl, heteroaryl, cycloalkyl and heterocyclyl,
A2 represents an optionally substituted group selected from alkyl, cycloalkyl, heterocyclyl, —(CH$_2$)$_n$-aryl and —(CH$_2$)$_n$-heteroaryl and
n represents 0, 1, 2 or 3.

R1, R2, R3 and R4 in said compounds are preferably hydrogen, $C_1$-$C_3$ alkyl, halogen, $C_1$-$C_3$ alkoxy, amino, $C_1$-$C_3$ alkylamino, $C_1$-$C_3$ dialkylamino. More preferably R1, R3, R4 are hydrogen; and R2 is hydrogen or methoxy. Most preferred are the compounds of this embodiment wherein R1, R3 and R4 are hydrogen and R2 is methoxy. R5 in said compounds is preferably $C_1$-$C_4$ alkyl, in particular methyl, and R6, R7, R8 and R9 are preferably selected from hydrogen, $C_1$-$C_3$ alkyl, halogen, $C_1$-$C_3$ alkoxy, amino, $C_1$-$C_3$ alkylamino, $C_1$-$C_3$ dialkylamino and hydroxyl, more preferably from hydrogen, halogen, $C_1$-$C_3$ alkoxy and hydroxyl. Most preferably R6, and R9 are hydrogen and R7 and R8 are independently hydrogen or methoxy.

G in said compounds is preferably a group —OCO$_2$(CH$_2$)$_n$-A1, with n being 0 or 1 and A1 optionally substituted aryl, heteroaryl, in particular pyridyl or phenyl, optionally substituted with halogen or methoxy; or
G is —OC(=O)CH$_2$-A2, —CH$_2$OC(=O)-A2, —CH$_2$OCO$_2$-A2, —CH$_2$NHCO$_2$-A2, —CH$_2$CO$_2$-A2, with A2 being optionally substituted alkyl, —(CH$_2$)$_n$-aryl, —(CH$_2$)$_n$-heteroaryl, in particular C$_1$-C$_4$ alkyl, with n being 0 or 1.

Another group of particularly preferred compounds of formula (I) are the compounds, wherein R2 represents a group —OR2a; and R2a represents hydrogen, formyl or an optionally substituted group selected from alkylcarbonyl, alkoxycarbonyl, arylcarbonyl and heteroarylcarbonyl, the optional substituents being e.g. selected from halogen, hydroxyl, C$_1$-C$_3$ alkoxy, amino, C$_1$-C$_3$ alkylamino, C$_1$-C$_3$ dialkylamino, cyano and carboxy.

Preferably, R2a represents an optionally substituted group selected from C$_1$-C$_4$ alkylcarbonyl, C$_1$-C$_4$alkoxycarbonyl and phenylcarbonyl in said group of compounds, more preferably a C$_1$-C$_4$ alkylcarbonyl group which is unsubstituted or substituted with a group —NR11R10, wherein
R11 represents C$_1$-C$_4$alkyl or, more preferably, hydrogen and
R10 represents hydrogen, C$_1$-C$_4$alkyl, C$_1$-C$_4$alkylcarbonyl or phenylcarbonyl.

R1, R3 and R4 are preferably hydrogen, C$_1$-C$_3$ alkyl, halogen, C$_1$-C$_3$ alkoxy, amino, C$_1$-C$_3$ alkylamino, C$_1$-C$_3$ dialkylamino or hydroxy in said group of compounds, most preferably hydrogen.

R5 is C$_1$-C$_4$ alkyl in said compounds, preferably methyl, and R6, R7, R8 and R9 are selected from hydrogen, C$_1$-C$_3$ alkyl, halogen, C$_1$-C$_3$ alkoxy, amino, C$_1$-C$_3$ alkylamino, C$_1$-C$_3$ dialkylamino and hydroxyl, preferably from hydrogen, halogen, C$_1$-C$_3$ alkoxy, and hydroxyl. Most preferably R6 and R9 are hydrogen and R7 and R8 are independently hydrogen or methoxy.

Further preferred specific embodiments of the compounds according to the invention are:
the compounds of formula (I), wherein
A1 represents an optionally substituted group selected from aryl, heteroaryl, cycloalkyl and heterocyclyl;
the compounds of formula (I), wherein
R2 represents a group —OR2a; and
R2a represents hydrogen, formyl or an optionally substituted group selected from alkylcarbonyl, alkoxycarbonyl, arylcarbonyl and heteroarylcarbonyl;
the compounds of formula (I), wherein
R2a represents hydrogen, C$_1$-C$_3$alkyl, formyl or an optionally substituted group selected from C$_1$-C$_4$alkylcarbonyl, C$_1$-C$_4$alkoxycarbonyl, C$_6$-C$_{10}$arylcarbonyl and C$_5$-C$_{10}$heteroarylcarbonyl;
A1 represents an optionally substituted group selected from C$_1$-C$_4$alkyl, C$_6$-C$_{10}$aryl, C$_5$-C$_{10}$heteroaryl, C$_3$-C$_7$cycloalkyl or C$_5$-C$_7$heterocyclyl; and
A2 represents an optionally substituted group selected from C$_1$-C$_4$alkyl, C$_3$-C$_7$cycloalkyl, C$_5$-C$_7$heterocyclyl, —(CH$_2$)$_n$—C$_6$-C$_{10}$aryl and —(CH$_2$)$_n$—C$_5$-C$_{10}$heteroaryl;
the compounds of formula (I), wherein
R1, R3 and R4 represent hydrogen;
the compounds of formula (I), wherein
R5 represents methyl;
the compounds of formula (I), wherein
R6, R7, R8 and R9 independently of one another represent: hydrogen, halogen, C$_1$-C$_3$ alkoxy or hydroxyl;
the compounds of formula (I), wherein
R6 and R9 both represent hydrogen and
R7 and R8 independently of one another represent hydrogen or methoxy; and
the compounds of formula (I), wherein optionally present substituents are selected from the group consisting of halogen, hydroxyl, C$_1$-C$_3$ alkoxy, amino, C$_1$-C$_3$ alkylamino, C$_1$-C$_3$ dialkylamino, cyano and carboxy.

the compounds of formula (I), wherein optionally present substituents are selected from the group consisting of C$_1$-C$_3$ alkyl and haloC$_1$-C$_3$ alkyl, in particular trifluoromethyl.

Also preferred are:
the compounds of formula (I), wherein
A1 represents an optionally substituted group selected from aryl, heteroaryl, cycloalkyl and heterocyclyl and
R2 represents hydrogen or, in particular, a group —OR2a; wherein R2a represents methyl;
the compounds of formula (I), wherein
A1 represents an optionally substituted group selected from aryl and heteroaryl;
A2 represents an optionally substituted group selected from alkyl, —(CH$_2$)$_n$-aryl and —(CH$_2$)$_n$-heteroaryl and
n represents 0 or 1, in particular, when
A1 is pyridyl or phenyl, optionally substituted with halogen or methoxy; and
A2 is C$_1$-C$_4$ alkyl.

Furthermore preferred are the compounds of formula (I) wherein
R2 represents a group —OR2a; and
R2a represents hydrogen, formyl or an optionally substituted group selected from alkylcarbonyl, alkoxycarbonyl, arylcarbonyl and heteroarylcarbonyl, in particular, when R2a is an optionally substituted group selected from C$_1$-C$_4$alkylcarbonyl, C$_1$-C$_4$alkoxycarbonyl and phenylcarbonyl.

A specific embodiment of these compounds are the compounds of formula (I), wherein R2a is a C$_1$-C$_4$alkylcarbonyl group which is unsubstituted or substituted with a group —NR11R10, wherein R11 is hydrogen or C$_1$-C$_4$alkyl, in particular hydrogen, and R10 is hydrogen, C$_1$-C$_4$alkyl, C$_1$-C$_4$alkylcarbonyl or phenylcarbonyl.

Another preferred embodiment of the compounds of formula (I) are the compounds, wherein
R2 represents a group —OR2a; and
R2a represents hydrogen, formyl or an optionally substituted group selected from alkylcarbonyl, alkoxycarbonyl, arylcarbonyl and heteroarylcarbonyl n represents 0 or 1 and
G is a group —OCO$_2$(CH$_2$)$_n$-A1, wherein
A1 represents an optionally substituted group selected from C$_1$-C$_4$alkyl, C$_6$-C$_{10}$aryl, C$_5$-C$_{10}$heteroaryl, C$_3$-C$_7$cycloalkyl or C$_5$-C$_7$heterocyclyl, in particular
a group —OCO$_2$(CH$_2$)$_n$-A1, wherein
n is 0 and A1 is C$_1$-C$_4$alkyl.

Particularly preferred are also compounds of formula (I) which have more than one of the features of the preferred embodiments of the compounds described above in combination.

For the purposes of this application the term "compound of formula (I)" is furthermore meant to refer to the free base or any acid addition salt thereof. Salts are especially the pharmaceutically acceptable salts of a compound of formula. I.

Such salts are formed, for example, as acid addition salts, preferably with organic or inorganic acids. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantane carboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methyl-benzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

The term "compound of formula (I)" is also meant herein to refer to hydrates and solvates, preferably pharmaceutically acceptable solvates, of these compounds.

The compounds of formula (I) according to the present invention and salts, solvates or hydrates thereof can be prepared according to known methods, as described herein or variations thereof that will be apparent to those skilled in the art, followed, if necessary, by removing any protecting groups, forming a pharmaceutically acceptable salt or forming a pharmaceutically acceptable solvate or hydrate.

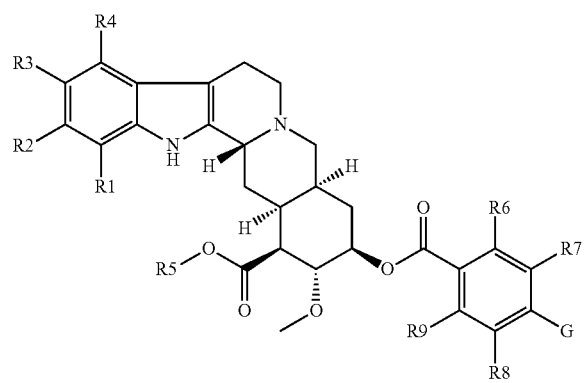

I

Compounds of formula (I) in which R1, R2 and R4 represent hydrogen can be prepared from reserpine (CAS 50-55-5) and its known derivatives by established methods.

Compounds of formula (I) in which R2 is not methoxy can be prepared using intermediates described in G. Varchi et al., J. Nat. Prod. 2005, 68, 1629-1631.

Compounds of formula (I) in which R1, R2 and R4 are not hydrogen can be prepared by total synthesis of the reserpine scaffold employing adequately substituted indole derivatives as starting materials by methods described e.g. in Swiss patent CH361811, Swiss patent CH364511, G. Stork et al., J. Am. Chem. Soc. 2005, 127, 16255-16262; S. Hanessian et al., J. Org. Chem. 1997, 62, 465-473; S. F. Martin et al., J. Am. Chem. Soc. 1985, 107, 4072-4074; S. F. Martin et al., J. Am. Chem. Soc. 1987, 109, 6124-6134.

Compounds in which R5 is not methyl can be prepared by methods as described in R. A. Lucas et al., J. Am. Chem. Soc. 1960, 82, 493-495; M. F. Bartlett, W. I. Taylor, Tetrahedron Lett. 1959, 20, 20-22.

More specifically, compounds of formula (I) can be obtained by a process in which a compound of formula (II)

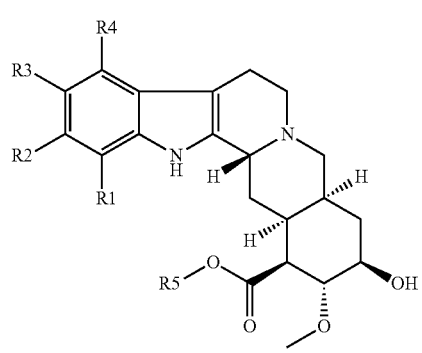

II reacts with an acid of formula (III)

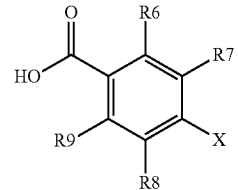

III or its corresponding acid chloride, using standard esterification conditions, and in which X represents G or a functional group which is further modified by known methods.

If X represents a group $-(CH_2)_n-X1$ and X1 represents hydroxyl or amino, compounds of formula (I) can be obtained by a process in which a compound of formula (IV)

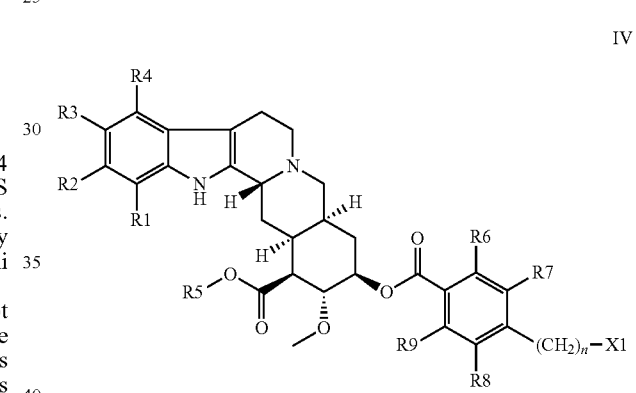

IV reacts with acids, acid chlorides, carbonates, chloroformates and the like by known methods.

Compounds of formula (I) in which R2 represents a group $-OR2a$ can be obtained by a process in which a compound of formula (V), which can be prepared according to G. Varchi et al., J. Nat. Prod. 2005, 68, 1629-1631,

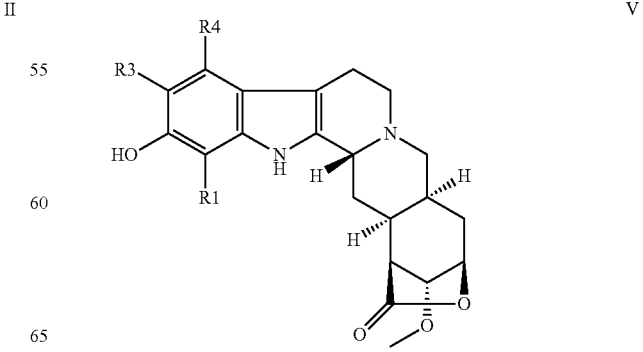

V is converted to the tert-butoxy carbonate of formula (VI) by known methods,

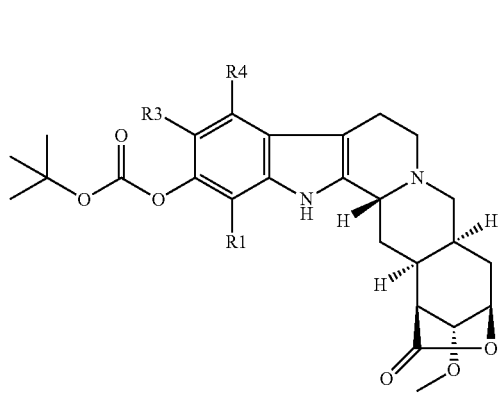

VI which is then treated with an alkoxide to give compounds of formula (VII),

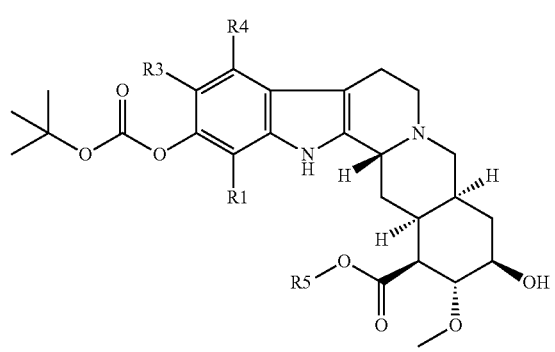

VII in which the free hydroxyl group can be modified as described above for compounds of formula (II), giving compounds of formula (VIII),

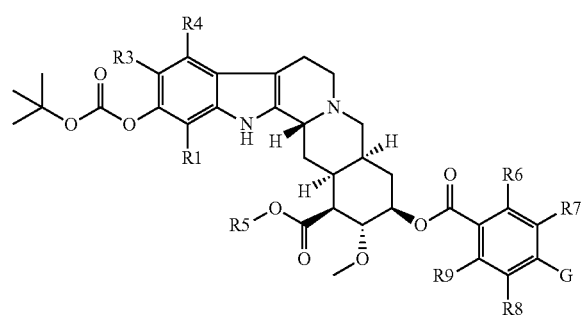

VIII

The tert-butoxy carbonate can be cleaved by known methods like treatment with acid, giving compounds of formula (IX),

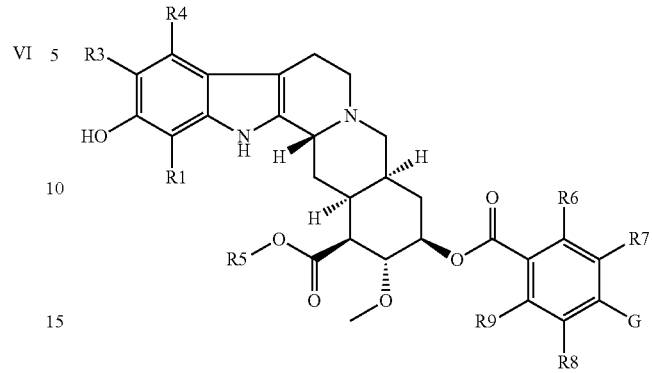

IX

Instead of the tert-butoxy carbonate, other known phenol protecting groups can also be used in this process.

Compounds of formula (IX) can react with alkylating or acylating agents by known methods to give compounds of formula (I) or their protected precursors.

As mentioned already above, the invention also relates to the use of a combination of a compound of formula (I)—with the exception of syrosingopine—and a mitochondrial inhibitor, e.g. metformin (and related biguanides, in particular phenformin and buformin), and to pharmaceutical products comprising a compound of formula (I)—with the exception of syrosingopine, in particular one of the preferred embodiments of compounds of formula (I) described above, and a mitochondrial inhibitor for use in the treatment of cancer, in particular for the treatment of carcinoma, leukemia, myeloma and lymphoma, and for achieving immunosuppression in autoimmunity, transplantation medicine and in other cases where immunosuppression is desirable, such as diseases of the skin, in particular psoriasis, nervous system, in particular multiple sclerosis, and of the haemopoietic system, in particular anemias; to the use of a combination of a compound of formula (I) and a mitochondrial inhibitor, e.g. metformin (and related biguanides like phenformin and buformin), for the preparation of a pharmaceutical composition for the treatment of cancer and achieving immunosuppression, and to methods of treatment of cancer and of achieving immunosuppression using a combination of a compound of formula (I) and a mitochondrial inhibitor, e.g. metformin (and related biguanides like phenformin and buformin), or pharmaceutical compositions comprising a compound of formula (I) and a mitochondrial inhibitor.

The invention relates furthermore to the use of a combination of a compound of formula (I) and a mitochondrial inhibitor, and of pharmaceutical compositions comprising a compound of formula (I) and a mitochondrial inhibitor for the treatment of cancer, in particular for the treatment of carcinoma, leukemia, myeloma, and lymphoma, and for the treatment of immunological disorders such as autoimmunity.

"Mitochondrial inhibitors" as understood in the present invention comprise compounds which reduce mitochondrial activity and demonstrate varying degrees of mitochondriotoxic properties. Mitochondrial inhibitors comprise so-called uncoupling agents, which uncouple the flow of protons from ATP synthesis in mitochondria, and inhibitors that target different complexes of the electron transfer chain (ETC) in mitochondria, e.g. complex I, complex II, complex III, complex IV, and complex V of the electron transfer chain. Further compounds considered to be mitochondrial inhibitors according to the invention are mitochondriotoxic compounds targeting the mitochondrial genome.

Many widely prescribed drugs exert side effects which are due to mitochondriotoxicity. These mitochondriotoxic drugs are also considered mitochondrial inhibitors according to the invention. Such mitochondriotoxic or mitochondrial inhibitory drugs synergize with a compound of formula (I) and represent anti-cancer agents when combined with a compound of formula (I). Mitochondriotoxic drugs have been used for treatment of very different clinical conditions (Cohen et al., Dev Disabil Res Rev 2010, 16:189-199). Mitochondrial inhibitors according to the invention comprise:

drugs used in liver or gallbladder disease with mitochondrial side effects, such as tetracycline, ibuprofen, amiodarone, pirprofen, tamoxifen, valproate, chloroquine, quinidine, chlorpromazine, ketoconazole, cyclosporine A, rifampicine, and glyburine;

inhibitors of electron transport chain complex I, such as amytal, capsaicin, haloperidol, risperidone, metformin, buformin, phenformin, bupivacaine, lidocaine, halothane, dantrolene, phenyloin, clofibrate, and fenofibrate;

inhibitors of electron transport chain complex II, such as cyclophosphamide and ketoconazole;

inhibitors of electron transport chain complex III, such as antimycin A, acetaminophen, isoflurane, and sevoflurane;

inhibitors of electron transport chain complex IV, such as cephaloridine, cefazolin, and cefalotin;

inhibitors of electron transport chain complex V, such as oligomycin;

inhibitors of mitochondrial DNA synthesis, such as AZT (itovudidine), d4T (stavudine), ddI (didanosine), and ddC (zalcitabine);

uncouplers of oxidative phosphorylation, such as pentamidine, indomethacin, fluoxetine, propofol, aspirin, bubivacaine, tolcapone, and dinitrophenol;

agents which reduce molecular oxygen to superoxide via a redox mechanism, such as doxorubicin, isoniazid, gentamycin, and fluoroquinolone; and inhibitors of mitochondrial gene transcription, such as interferon-alpha and interferon-gamma.

Metformin is 3-(diaminomethylidene)-1,1-dimethyl-guanidine:

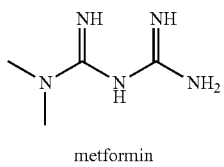

metformin

Other biguanides considered are, for example, phenformin or buformin, preferably phenformin.

Phenformin is 1-(diaminomethylidene)-2-(2-phenylethyl)guanidine:

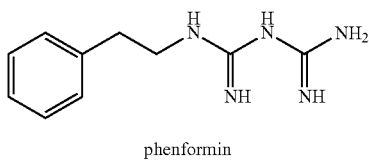 [SMILES: N=C(N)NC(=N)NCCc1ccccc1]

phenformin

In view of the close relationship between basic compounds and their acid addition salts, metformin, phenformin and other mitochondrial inhibitors having basic nitrogen atoms mean the free base or any acid addition salt thereof.

Such salts are formed, for example, as acid addition salts, preferably with organic or inorganic acids. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantane carboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methyl-benzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

The invention also relates to a pharmaceutical product comprising a compound of formula (I) as described above—with the exception of syrosingopine- and a mitochondrial inhibitor.

Said pharmaceutical products may comprise one or more than one dosage unit comprising a compound of formula (I) and one or more than one dosage unit comprising a mitochondrial inhibitor.

A pharmaceutical product according to the present invention can also comprise one or more than one dosage unit, wherein each of said dosage units comprises both, a compound of formula (I) and a mitochondrial inhibitor.

Another embodiment of the invention is a pharmaceutical product which is free of mitochondrial inhibitors and which comprises a compound of formula (I)—with the exception of syrosingopine—and means for providing instructions for use of said pharmaceutical product, wherein said instructions for use include an instruction to use the pharmaceutical product in combination with a medicament comprising a mitochondrial inhibitor.

Yet another embodiment of the invention is a pharmaceutical product comprising a mitochondrial inhibitor and means for providing instructions for use of said pharmaceutical product, wherein said instructions for use include an instruction to use the pharmaceutical product in combination with a medicament comprising a compound of formula (I) with the exception of syrosingopine. A specific embodiment of this product is free of compounds of formula (I).

Means for providing instructions for the use of said product include, in particular, a package of the product and/or a package insert, on which the instructions are printed.

Preferred are pharmaceutical products according to the invention comprising one or more than one dosage unit, wherein each of said dosage units comprises both, a compound of formula (I) and a mitochondrial inhibitor, i.e. fixed combinations of said components.

These products include pharmaceutical compositions comprising a compound of formula (I) and a mitochondrial inhibitor and are, for example, compositions for enteral administration, such as nasal, buccal, rectal or, especially, oral administration, and for parenteral administration, such as intravenous, intramuscular or subcutaneous administration. The compositions may comprise a compound of formula (I) and a mitochondrial inhibitor, e.g. metformin, alone or, preferably, together with a pharmaceutically acceptable carrier.

The dosage of the combination of a compound of formula (I) and the mitochondrial inhibitor depends upon the disease to be treated and upon the species, its age, weight, and individual condition, the individual pharmacokinetic data, and the mode of administration.

The pharmaceutical compositions comprise from approximately 1% to approximately 95% of the combination of a compound of formula (I) and a mitochondrial inhibitor, e.g. metformin, single-dose administration forms comprising in the preferred embodiment from approximately 20% to approximately 90% combination of a compound of formula (I) and a mitochondrial inhibitor, and forms that are not of single-dose type comprising in the preferred embodiment from approximately 5% to approximately 20% combination of a compound of formula (I) and mitochondrial inhibitor. Unit dose forms are, for example, coated and uncoated tablets, ampoules, vials, suppositories, or capsules. Further dosage forms are, for example, ointments, creams, pastes, foams, tinctures, drops, sprays, and dispersions. Examples are capsules containing from about 0.05 g to about 1.0 g combination of a compound of formula (I) and mitochondrial inhibitor.

The pharmaceutical compositions of the present invention are prepared in a manner known per se, for example by means of conventional mixing, granulating, coating, dissolving or lyophilizing processes.

Preference is given to the use of solutions of the combination of a compound of formula (I) and a mitochondrial inhibitor, e.g. metformin, and also suspensions or dispersions, especially isotonic aqueous solutions, dispersions or suspensions which, for example in the case of lyophilized compositions comprising the combination of a compound of formula (I) and a mitochondrial inhibitor, alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers for preferred solid oral dosage forms are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of the combination of a compound of formula (I) and mitochondrial inhibitor.

Pharmaceutical compositions for oral administration also include hard capsules consisting of gelatin, and also soft, sealed capsules consisting of gelatin and a plasticizer, such as glycerol or sorbitol. The hard capsules may contain the combination of a compound of formula (I) and mitochondrial inhibitor in the form of granules, for example in admixture with fillers, such as corn starch, binders, and/or glidants, such as talc or magnesium stearate, and optionally stabilizers. In soft capsules, the combination of a compound of formula (I) and mitochondrial inhibitor is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of a compound of formula (I) and a mitochondrial inhibitor, e.g. metformin, and a suppository base. Suitable suppository bases are, for example, natural or synthetic triglycerides, paraffin hydrocarbons, polyethylene glycols or higher alkanols.

For parenteral administration, aqueous solutions of a combination of a compound of formula (I) and a mitochondrial inhibitor, or aqueous injection suspensions that contain viscosity-increasing substances, for example sodium carboxymethylcellulose, sorbitol and/or dextran, and, if desired, stabilizers, are especially suitable. The combination of a compound of formula (I) and mitochondrial inhibitor, optionally together with excipients, can also be in the form of a lyophilizate and can be made into a solution before parenteral administration by the addition of suitable solvents. Solutions such as are used, for example, for parenteral administration can also be employed as infusion solutions.

Preferred preservatives are, for example, antioxidants, such as ascorbic acid, or microbicides, such as sorbic acid or benzoic acid.

The combinations according to the invention of a mitochondrial inhibitor, e.g. metformin, and a compound of formula (I), and pharmaceutical compositions comprising a mitochondrial inhibitor and a compound of formula (I) according to the invention show therapeutic efficacy against different types of cancer including carcinomas, sarcomas, gliomas, leukemias, lymphomas, e.g. epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ductal-, lobular and medullary neoplasms, acinar cell neoplasms, complex epithelial neoplasms, specialized gonadal neoplasms, paragangliomas and glomus tumors, naevi and melanomas, soft tissue tumors including sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, gliomas, glioblastomas, oligodendrogliomas, neuroepitheliomatous neoplasms, meningiomas, nerve sheath tumors, granular cell tumors and alveolar soft part sarcomas, Hodgkin's and non-Hodgkin's lymphomas, other lymphoreticular neoplasms, plasma cell tumors, mast cell tumors, immunoproliferative diseases, leukemias including acute and chronic leukemias, miscellaneous myeloproliferative disorders, lymphoproliferative disorders and myelodysplastic syndromes.

The combinations according to the invention of a mitochondrial inhibitor, e.g. metformin, and a compound of formula (I), and pharmaceutical compositions comprising a mitochondrial inhibitor and a compound of formula (I) according to the invention show also therapeutic efficacy against immunological diseases sensitive to blockade of T cell proliferation including connective tissue diseases such as lupus erythematodes, sclerodermia, polymyositis/dermatomyositis, mixed connective tissue disease, rheumatoid arthritis, Sjögren-syndrome, panarteriitis nodosa, Wegeners granulomatosis; systemic autoimmune diseases such as rheumatoid arthritis, Goodpasture's syndrome, Wegener's granulomatosis, polymyalgia rheumatica, Guillain-Barré syndrome, multiple sclerosis; localized autoimmune diseases such as type 1 diabetes mellitus, Hashimoto's thyroiditis, Graves' disease, celiac disease, Crohn's disease, ulcerative colitis, Addison's disease, primary biliary cirrhosis, autoimmune hepatitis, and giant cell arteritis.

The combination of the mitochondrial inhibitor and the compound of formula (I) according to the invention and a pharmaceutical compositions comprising a compound of formula (I) and a mitochondrial inhibitor, e.g. metformin, according to the invention may be applied in the form of fixed combinations. Such fixed combination may contain a compound of formula (I) and a mitochondrial inhibitor, e.g. metformin, in a relative amount (weight per weight) of between 1 to 10 and 1 to 1,000, preferably between 1 to 100 and 1 to 200, such as a combination of 1 to 130, with the maximum recommended daily dose of metformin being based on the experience with its use in diabetes type 2 therapy. Alternatively, a covalent linkage between a compound of formula (I) and some of the mitochondrial inhibitors, e.g. metformin, may be envisaged.

Alternatively, the combination of a compound of formula (I) and a mitochondrial inhibitor, e.g. metformin, may be applied in two different, separate pharmaceutical compositions, optionally being provided together in a kit. The administration of the compound of formula (I) and the mitochondrial inhibitor, e.g. metformin, can be administered simultaneously or a compound of formula (I) is administered separately before or after the mitochondrial inhibitor. Furthermore, the compounds may be given independently of one another within a reasonable time window. A treatment of cancer or autoimmune diseases or in an immunosuppressive treatment with a separate medicament containing a compound of formula (I) in combination with another approved medicament containing a mitochondrial inhibitor, like e.g. a commercially available metformin-containing medicament for the treatment type-2 diabetes, is another specific embodiment of the present invention.

Pharmaceutical compositions comprising a compound of formula (I) and a mitochondrial inhibitor, e.g. metformin, may be further combined with other chemotherapeutic agents. Therapeutic agents for possible combination are especially one or more cytostatic or cytotoxic compounds, for example a chemotherapeutic agent or several selected from the group comprising indarubicin, cytarabine, interferon, hydroxyurea, bisulfan, or an inhibitor of polyamine biosynthesis, an inhibitor of the mTOR pathway, an inhibitor of mTOR-complex 1 or mTOR complex 2, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, an inhibitor of the interaction of an SH2 domain with a phosphorylated protein, an inhibitor of Bcl-2 and modulators of the Bcl-2 family members such as Bax, Bid, Bad, Bim, Nip3 and BH3-only proteins.

The combination of a compound of formula (I) and mitochondrial inhibitors, e.g. metformin, and pharmaceutical compositions comprising a compound of formula (I) and mitochondrial inhibitors may be administered especially for cancer therapy in combination with radiotherapy, immunotherapy, surgical intervention, or a combination of these. Long-term therapy is equally possible as is adjuvant therapy in the context of other treatment strategies or neo-adjuvant therapy in combination with surgery. Other possible treatments are therapy to maintain the patient's status after tumor regression, or chemopreventive therapy, for example in patients at risk.

The present invention relates furthermore to a method for the treatment of cancer and of immunological disorders such as autoimmunity, which comprises administering a combination of a compound of formula (I) and a mitochondrial inhibitor, e.g. metformin, in a quantity effective against said disease, to a warm-blooded animal requiring such treatment. The combination of a compound of formula (I) and mitochondrial inhibitors, e.g. metformin, can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 3 g, preferably from approximately 0.25 g to approximately 1.5 g, of a combination of the present invention.

The invention also relates to the use of a combination of a compound of formula (I) and a mitochondrial inhibitor, e.g. metformin, and of pharmaceutical compositions comprising a compound of formula (I) and a mitochondrial inhibitor for the treatment of cancer, in particular for the treatment of the particular cancers mentioned above. More specifically, the invention relates to the use of a combination of a compound of formula (I) and a mitochondrial inhibitor and of pharmaceutical compositions comprising a compound of formula (I) and a mitochondrial inhibitor for the treatment of carcinomas, sarcomas, leukemias, myelomas, lymphomas, and cancers of the nervous system. Furthermore, the invention relates to the use of a combination of a compound of formula (I) and a mitochondrial inhibitor and of pharmaceutical compositions comprising a compound of formula (I) and a mitochondrial inhibitor for achieving immunosuppression in autoimmunity, transplantation medicine and in other cases where immunosuppression is desirable, in particular in immunological diseases sensitive to blockade of T cell proliferation, systemic autoimmune diseases, and localized autoimmune diseases, as explained above. More specifically, the invention relates to the use of a combination of a compound of formula (I) and a mitochondrial inhibitor, e.g. metformin, and of pharmaceutical compositions comprising a compound of formula (I) and a mitochondrial inhibitor for the treatment of autoimmune diseases, such as autoimmune diseases of the skin, nervous system, connective tissue, muscle, nervous system, blood forming system, bone and inner organs, in particular psoriasis, multiple sclerosis, and anemias.

The preferred relative amount of a compound of formula (I) and mitochondrial inhibitor, e.g. metformin, dose quantity and kind of pharmaceutical composition, which are to be used in each case, depend on the type of cancer or autoimmune disease, the severity and progress of the disease, and the particular condition of the patient to be treated, and has to be determined accordingly by the physician responsible for the treatment.

Further specific aspects of the present invention include the following:
- a compound of formula (I) as described above—with the exception of syrosingopine—for a use in the treatment of cancer or autoimmune diseases or in an immunosuppressive treatment in combination with a mitochondrial inhibitor or a mitochondrial inhibitor for a use in said treatments in combination with a compound of formula (I) as described above—with the exception of syrosingopine, wherein the mitochondrial inhibitor comprises or is metformin, buformin or phenformin, in particular metformin;
- a compound of formula (I) as described above—with the exception of syrosingopine—for a use in the treatment of cancer or autoimmune diseases or in an immunosuppressive treatment in combination with a mitochondrial inhibitor or a mitochondrial inhibitor for a use in said treatments in combination with a compound of formula (I) as described above—with the exception of syrosingopine, wherein the mitochondrial inhibitor is selected from rotenone, piericidin A, epiberberine, 2-thenoyltrifluoroacetone (TTFA), antimycin A, oligomycin, carbonyl cyanide-p-trifluoromethoxyphenylhydrazone (FCCP), and stavudine;
- a compound of formula (I) as described above—with the exception of syrosingopine—for a use in the treatment of cancer or autoimmune diseases or in an immunosuppressive treatment in combination with a mitochondrial inhibitor or a mitochondrial inhibitor for a use in said treatments in combination with a compound of formula (I) as described above—with the exception of syrosingopine, wherein the mitochondrial inhibitor comprises or is oligomycin;
- a compound of formula (I) as described above—with the exception of syrosingopine—for a use in the treatment of cancer or autoimmune diseases or in an immunosuppressive treatment in combination with a mitochondrial inhibitor or a mitochondrial inhibitor for a use in said treatments in combination with a compound of formula (I) as described above—with the exception of syrosingopine, wherein the relative dosage (weight per weight) of the compound of formula (I) and the mitochondrial inhibitor is between 1 to 10 and 1 to 1,000, preferably between 1 to 10 and 1 to 500, e.g. between 1 to 10 and 1 to 200;
- a compound of formula (I) as described above—with the exception of syrosingopine—for a use in the treatment of cancer or autoimmune diseases or in an immunosuppressive treatment in combination with a mitochondrial inhibitor or a mitochondrial inhibitor for a use in said treatments in combination with a compound of formula (I) as described above—with the exception of syrosingopine, wherein the mitochondrial inhibitor is metformin and the relative dosage (weight per weight) of the compound of formula (I) and the metformin is between 1 to 10 and 1 to 200;
- a compound of formula (I) as described above—with the exception of syrosingopine—for a use in the treatment of cancer or autoimmune diseases or in an immunosuppressive treatment in combination with a mitochondrial inhibitor or a mitochondrial inhibitor for a use in said treatments in combination with a compound of formula (I) as described above—with the exception of syrosingopine, wherein the mitochondrial inhibitor is oligomycin and the relative dosage (weight per weight) of the compound of formula (I) and the oligomycin is between 1,000 to 1 and 10,000 to 1;
- a compound of formula (I) as described above—with the exception of syrosingopine—for a use in the treatment of cancer or autoimmune diseases or in an immunosuppressive treatment in combination with a mitochondrial inhibitor or a mitochondrial inhibitor for a use in said treatments in combination with a compound of formula (I) as described above—with the exception of syrosingopine, wherein the cancer is selected from carcinoma, sarcoma, leukemia, myeloma, lymphoma, and cancers of the nervous system;
- a compound of formula (I) as described above—with the exception of syrosingopine—for a use in an immunosuppressive treatment in combination with a mitochondrial inhibitor or a mitochondrial inhibitor for a use in said treatment in combination with a compound of formula (I) as described above—with the exception of syrosingopine;
- a compound of formula (I) as described above—with the exception of syrosingopine—for a use in the treatment of autoimmune diseases of the skin, nervous system, connective tissue, muscle, nervous system, blood forming system, bone and inner organs in combination with a mitochondrial inhibitor or a mitochondrial inhibitor for a use in said treatments in combination with a compound of formula (I) as described above—with the exception of syrosingopine;
- a compound of formula (I) as described above—with the exception of syrosingopine—for a use in the treatment of cancer or autoimmune diseases or in an immunosuppressive treatment in combination with a mitochondrial inhibitor or a mitochondrial inhibitor for a use in said treatments in combination with a compound of formula (I) as described above—with the exception of syrosingopine, wherein the compound of formula (I) is administered separately before or after administration of the mitochondrial inhibitor;
- a compound of formula (I) as described above—with the exception of syrosingopine—for a use in the treatment of cancer or autoimmune diseases or in an immunosuppressive treatment in combination with a mitochondrial inhibitor or a mitochondrial inhibitor for a use in said treatments in combination with a compound of formula (I) as described above—with the exception of syrosingopine, wherein the compound of formula (I) and the mitochondrial inhibitor are administered together or simultaneously; and
- a compound of formula (I) as described above, with the proviso that R2 in formula (I) must not be hydrogen or methoxy, when A1 is alkyl, for a use in the treatment of cancer or autoimmune diseases or in an immunosuppressive treatment in combination with a mitochondrial inhibitor or a mitochondrial inhibitor for a use in said treatments in combination with a compound of formula (I) as described above, with the proviso that R2 in formula (I) must not be hydrogen or methoxy, when A1 is alkyl.

Further specific embodiments of the pharmaceutical products according to the present invention mentioned already above include e.g. such products, wherein
- the mitochondrial inhibitor is selected from metformin, buformin, phenformin, rotenone, piericidin A, epiberberine, 2-thenoyltrifluoroacetone (TTFA), antimycin A, carbonyl cyanide-p-trifluoromethoxyphenylhydrazone (FCCP), and stavudine and the relative amount (weight per weight) of the compound of formula (I) and mitochondrial inhibitor is between 1 to 10 and 1 to 1000, preferably between 1 to 10 and 1 to 500, e.g. between 1 to 10 and 1 to 200;
- the mitochondrial inhibitor is metformin and the relative amount (weight per weight) of compound of formula (I) and metformin is between 1 to 10 and 1 to 200; and
- the mitochondrial inhibitor is oligomycin and the relative amount (weight per weight) of compound of formula (I) and oligomycin is between 1,000 to 1 and 10,000 to 1.

A further aspect of the present invention is a pharmaceutical product as described herein for use in the treatment of cancer or autoimmune diseases or in an immunosuppressive treatment.

The invention further relates to the use of a combination of a compound of formula (I)—with the exception of syrosingopine- and a mitochondrial inhibitor, e.g. metformin, for the preparation of a pharmaceutical composition for the treatment of cancer or autoimmune disease, as explained above, as well as to the use of a—with the exception of syrosingopine—for the manufacture of a medicament for use in the treatment of cancer or autoimmune diseases or in an immunosuppressive treatment in combination with a mitochondrial inhibitor or to the use of a mitochondrial inhibitor, e.g. metformin, for the manufacture of a medicament for use in the treatment of cancer or autoimmune diseases or in an immunosuppressive treatment in combination with a—with the exception of syrosingopine.

Especially, the invention provides a method for treatment of cancer or autoimmune disease, which comprises administering a combination of a compound of formula (I) and a mitochondrial inhibitor, e.g. metformin, or of a pharmaceutical composition comprising a compound of formula (I) and a mitochondrial inhibitor, in a quantity effective against said disease, to a warm-blooded animal requiring such treatment. Particularly preferred is treatment of a human.

The invention further relates to a method for the determination whether a cancerous cell is responsive to a compound of formula (I) treatment comprising the steps of
(a) preparation of single cell suspension and culturing the cancerous cell in a suitable media,
(b) incubating the cancerous cell with a compound of formula (I)—with the exception of syrosingopine,
(c) incubating the cancerous cell of step (b) with a positively charged fluorescent dye,
(d) measuring the excitation fluorescence intensity, and
(e) comparing the measured fluorescence intensity of step (d) with the measured fluorescence intensity of the cancerous cell incubated with the positively charged fluorescent dye alone,
and wherein a relative increase of fluorescence intensity of cancerous cells pre-incubated with a compound of formula (I) indicates a compound of formula (I) treatment responsiveness. For practical purposes the cancerous cell is a cell isolated from a potential patient to be treated with a combination of a compound of formula (I) and a mitochondrial inhibitor. Suitable media for culturing such cancerous cells are well known in the art, and include, for example Iscoves modified Dulbecco medium (IMDM) or RPMI 1640 medium. Prior to testing, a single cell suspension from the ex vivo tumor material has to be prepared. Again, suitable standardized commercial methodologies are at hand, where physical disruption and enzymatic digestion steps are combined (see for example the methods by MiltenyiBiotec or by Invitrogen). For testing, it is advisable to preincubate the cancerous cell with different concentrations of a compound of formula (I), e.g. 0.1 µM and 10 µM, for 2 to 8 h. A suitable positively charged fluorescent dye is TMRM (tetramethylrhodamine methyl ester perchlorate). Other positively charged fluorescent dyes considered are the rhodamines TMRE (tetramethylrhodamine ethyl ester perchlorate), Rhodamine 123 (rhodamine methyl ester chloride), Rhodamine B (tetraethylrhodamine hydrochloride), MitoTracker Red CMXRos® (CAS designation 1H,5H,11H,15H-xantheno[2,3,4-ij:5,6,7-i'j']diquinolizin-18-ium, 9-[4-(chloromethyl)phenyl]-2,3,6,7,12,13,16,17-octahydro-, chloride), and the carbocyanines JC-1 (5,5',6,6'-tetrachloro-1,1',3,3'-tetraethylbenzimidazolocarbocyanine iodide) and $DiOC_6(3)$ (3,3'-dihexylbenzoxazolocarbocyanine iodide).

Staining with the preferred fluorescent dye TMRM (tetramethylrhodamine methyl ester) is preferably done according to standard methods, such as indicated by the supplier Serotec. Fluorescence is measured at 575 nm after excitation at 488 nm, preferably in a standard commercially available flow cytometer.

If the cancerous cell shows responsiveness to a compound of formula (I), the corresponding patient will probably be effectively treated by combinations of a compound of formula (I) and a mitochondrial inhibitor. If the cancerous cell is not responsive to a compound of formula (I) in the corresponding fluorescence test with TMRM, chances are low that the patient can be effectively treated with combinations of a compound of formula (I) and a mitochondrial inhibitor.

EXAMPLES

Particular embodiments of the invention are described in the following Examples, which serve to illustrate the invention in more detail.

General Comments:

All reagents and solvents are of commercial quality and used without further purification unless otherwise noted; reactions are routinely performed with anhydrous solvents in well-dried glassware under an argon or nitrogen atmosphere; evaporations are carried out by rotary evaporation under reduced pressure and work-up procedures are carried out after removal of residual solids by filtration;

all temperatures are given in ° C.; unless otherwise noted, operations are carried out at room temperature, that is typically in the range of 15-30° C.;

column chromatography (by the flash procedure) is used to purify compounds and is performed using Merck silica gel 60 (70-230 mesh ASTM) unless otherwise stated; in general, the course of reactions is followed by TLC, HPLC, or LC/MS and reaction times are given for illustration only; yields are given for illustration only and are not necessarily the maximum attainable;

the structure of the final products of the invention is generally confirmed by NMR and mass spectral techniques. Proton NMR spectra are recorded on a Brucker 400 MHz spectrometer or a Varian Mercury Plus 400 MHz spectrometer. Chemical shifts (δ) are reported in ppm relative to $Me_4Si$ or solvent peaks as internal standard, and J values are in Hertz (Hz). Each peak is denoted as a broad singlet (br), singlet (s), doublet (d), triplet (t), doublet of doublets (dd), triplet of doublets (td) or multiplet (m). Mass spectra are generated using a q-T of Ultima (Waters AG) mass spectrometer or an Agilent 1100 Series MS spectrometer in the positive ESI mode;

each intermediate is purified to the standard required for the subsequent stage and is characterized in sufficient detail to confirm that the assigned structure is correct; analytical and preparative HPLC on non-chiral phases are performed using RP-C18 based columns;

the following abbreviations may be used:
Acetone-d6: Deuterated acetone
$CDCl_3$: Deuterated chloroform
$CD_3OD$: Deuterated methanol
DCC: N,N'-Dicyclohexylcarbodiimide
DCM: Dichloromethane
DMAP: 4-(Dimethylamino)pyridine
DMF: N,N-Dimethylformamide
DMSO-d6: Deuterated dimethyl sulphoxide
$D_2O$: Deuterated water
ELSD: Evaporative light scattering detection
HPLC: High performance liquid chromatography
J: Coupling constant
LC/MS: Liquid chromatography coupled to mass spectoscopy
$Me_4Si$: Tetramethylsilane
MS: Mass spectroscopy
NMR: Nuclear magnetic resonance
4-PPY: 4-Pyrrolidinopyridine
TFA: Trifluoroacetic acid
THF: Tetrahydrofuran
TLC: Thin layer chromatography

Example 1

(a) Preparation of methyl (1R,15S,17R,18R,19S,20S)-17-[(4-formylphenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate

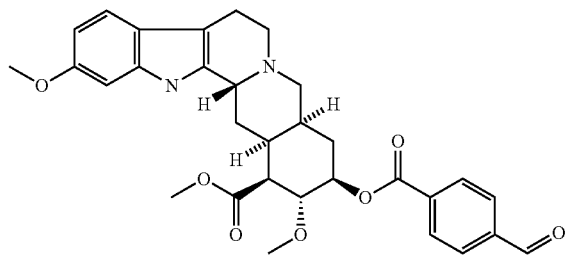 [SMILES: COC(=O)[C@H]1[C@H]2C[C@@H]3c4[nH]c5cc(OC)ccc5c4CCN3C[C@H]2C[C@@H](OC(=O)c2ccc(C=O)cc2)[C@@H]1OC]

Under nitrogen atmosphere, 500 mg of methyl (1R,15S,17R,18R,19S,20S)-17-hydroxy-6,18-dimethoxy-3,13-diazapentacyclo[11.8.0.0$^{2,10}$.0$^{4,9}$.0$^{15,20}$]henicosa-2(10),4,6,8-tetraene-19-carboxylate (CAS 2901-66-8) (1.21 mmol, 1.0 eq.), 543 mg of 4-formylbenzoic acid (3.62 mmol, 3.0 eq.), 747 mg of DCC (3.62 mmol, 3.0 eq.) and 54 mg of 4-PPY (0.36 mmol, 0.3 eq.) are dissolved in 50 mL of DCM. After agitation at 15° C. for 20 hours, the reaction mixture is filtered and the filtrate is concentrated under reduced pressure. The residue is purified by silica gel column chromatography (eluent: ethyl acetate/petroleum ether=4/1 v/v-ethyl acetate/petroleum ether/acetone=4/1/1 v/v/v) to give 500 mg of the desired product as light yellow solid.

MS m/z (+ESI): 547.2 [M+H]$^+$ (b) Preparation of methyl (1R,15S,17R,18R,19S,20S)-17-{[4-(hydroxymethyl)phenyl]carbonyloxy}-6,18-dimethoxy-3,13-diazapentacyclo[11.8.0.0$^{2,10}$.0$^{4,9}$.0$^{15,20}$]henicosa-2(10),4,6,8-tetraene-19-carboxylate

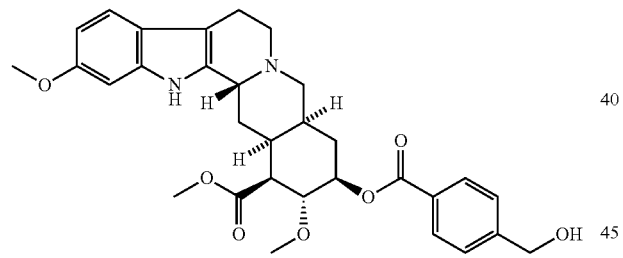

Under N$_2$ atmosphere, 480 mg of methyl (1R,15S,17R,18R,19S,20S)-17-[(4-formylphenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate (0.88 mmol, 1.0 eq.) are dissolved in 15 mL of THF and 30 mL of ethanol. Then 143 mg of NaBH$_4$ (3.78 mmol, 4.3 eq.) are added at 0° C. After agitation at 0-5° C. for 2 hours, the reaction mixture is filtered and the filtrate is directly purified by preparative HPLC (eluent: water with 0.1% formic acid and acetonitrile; gradient) to give 380 mg of the desired product as white solid (formic acid salt).

$^1$H NMR (400 MHz, DMSO-d$_6$) δ ppm: 10.52 (s, 1H), 8.03 (d, J=8.4 Hz, 2H), 7.50 (d, J=8.4 Hz, 2H), 7.23 (d, J=8.4 Hz), 6.81 (d, J=2.4 Hz, 1H), 6.62 (dd, J$_{1=2.4}$ Hz and J$_2$=8.4 Hz, 1H), 5.40 (t, J=5.6 Hz, 1H), 4.95 (m, 1H), 4.61 (d, J=5.6 Hz, 2H), 4.35 (m, 1H), 3.89 (dd, J$_1$≈, J$_2$=10.0 Hz, 1H), 3.80 (s, 3H), 3.76 (s, 3H), 3.40 (s, 3H), 3.10-1.75 (m, 13H).

MS m/z (+ESI): 549.3 [M+H]$^+$ (c) Preparation of methyl (1R,15S,17R,18R,19S,20S)-17-({4-[(acetyloxy)methyl]phenyl}carbonyloxy)-6,18-dimethoxy-3,13-diazapentacyclo[11.8.0.0$^{2,10}$.0$^{4,9}$.0$^{15,20}$]henicosa-2(10),4,6,8-tetraene-19-carboxylate

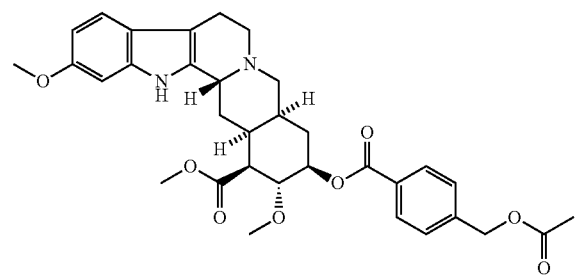 [SMILES: COC(=O)[C@H]1[C@H]2C[C@@H]3c4[nH]c5cc(OC)ccc5c4CCN3C[C@H]2C[C@@H](OC(=O)c2ccc(COC(C)=O)cc2)[C@@H]1OC]

Under N$_2$ atmosphere, 100 mg of methyl (1R,15S,17R,18R,19S,20S)-17-{[4-(hydroxymethyl)phenyl]carbonyloxy}-6,18-dimethoxy-3,13-diazapentacyclo[11.8.0.0$^{2,10}$.0$^{4,9}$.0$^{15,20}$]henicosa-2(10),4,6,8-tetraene-19-carboxylate (0.18 mmol, 1.0 eq.) are dissolved in 6 mL of pyridine. Then 3 mg of 4-PPY (0.02 mmol, 0.11 eq.) and 186 mg of acetic anhydride (1.82 mmol, 10 eq.) are added. After agitation at 15° C. for 20 hours, the reaction mixture is concentrated under reduced pressure and the residue is purified by preparative HPLC (eluent: water with 0.1% formic acid and acetonitrile; gradient) to give 64 mg of the desired product as off-white solid (formic acid salt).

$^1$H NMR (400 MHz, DMSO-d$_6$) δ ppm: 10.54 (s, 1H), 8.06 (d, J=8.4 Hz, 2H), 7.55 (d, J=8.4 Hz, 2H), 7.23 (d, J=8.4 Hz, 1H), 6.81 (d, J=2.0 Hz, 1H), 6.62 (dd, J$_1$=8.4 Hz and J$_2$=2.0 Hz, 1H), 5.19 (s, 2H), 4.97 (m, 1H), 4.35 (s, 1H), 3.89 (dd, J$_1$=9.6 Hz and J$_2$=10.8 Hz, 1H), 3.80 (s, 3H), 3.76 (s, 3H), 3.40 (s, 3H), 3.10-1.75 (m, 13H), 2.12 (s, 3H).

MS m/z (+ESI): 591.1 [M+H]$^+$

Example 2

Preparation of methyl (1R,15S,17R,18R,19S,20S)-17-[(4-{[(ethoxycarbonyl)oxy]methyl}phenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate

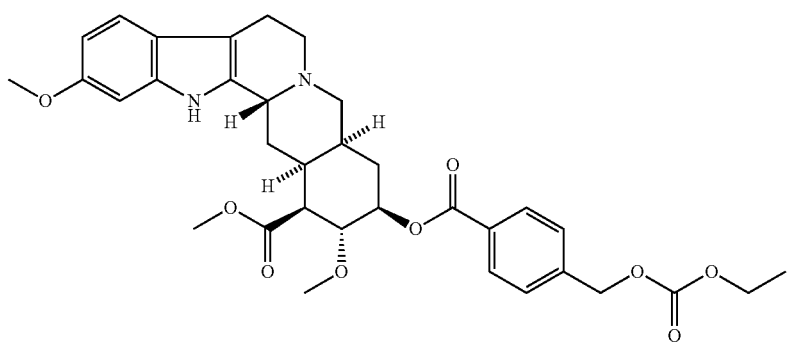 [SMILES: CCOC(=O)OCc1ccc(C(=O)O[C@@H]2C[C@@H]3CN4CCc5c([nH]c6cc(OC)ccc56)[C@H]4C[C@@H]3[C@H](C(=O)OC)[C@H]2OC)cc1]

Under N$_2$ atmosphere, 100 mg of methyl (1R,15S,17R, 18R,19S,20S)-17-{[4-(hydroxymethyl)phenyl]carbonyloxy}-6,18-dimethoxy-3,13-diazapentacyclo[11.8.0.0$^{2,10}$.0$^{4,9}$.0$^{15,20}$]henicosa-2(10),4,6,8-tetraene-19-carboxylate (0.18 mmol, 1.0 eq.) are dissolved in 6 mL of pyridine. Then 396 mg of ethyl chloroformate (3.65 mmol, 20 eq.) are added dropwise at 0° C. After agitation at this temperature for 30 min, the reaction mixture is diluted with 4 mL of methanol and concentrated under reduced pressure. The residue is purified by preparative HPLC (eluent: water with 0.1% formic acid and acetonitrile; gradient) to give 90 mg of the desired product as off-white solid (formic acid salt).

$^1$H NMR (400 MHz, DMSO-d$_6$) δ ppm: 10.60 (br, 1H), 8.08 (d, J=8.4 Hz, 2H), 7.56 (d, J=8.4 Hz, 2H), 7.25 (d, J=8.4 Hz, 1H), 6.82 (s, 1H), 6.63 (d, J=8.4 Hz, 1H), 5.25 (s, 2H), 4.97 (m, 1H), 4.40 (m, 1H), 4.18 (q, J=7.2 Hz, 2H), 3.89 (dd, J$_1$≈J$_2$=10.4 Hz, 1H), 3.80 (s, 3H), 3.76 (s, 3H), 3.40 (s, 3H), 3.20-1.75 (m), 1.24 (t, J=7.2 Hz, 3H).

MS m/z (+ESI): 621.2 [M+H]$^+$

Example 3

Preparation of methyl (1R,15S,17R,18R,19S,20S)-17-{[4-({[(tert-butoxy)carbonyl]amino}methyl)phenyl]carbonyloxy}-6,18-dimethoxy-3,13-diazapentacyclo[11.8.0.0$^{2,10}$.0$^{4,9}$.0$^{15,20}$]henicosa-2(10),4,6,8-tetraene-19-carboxylate

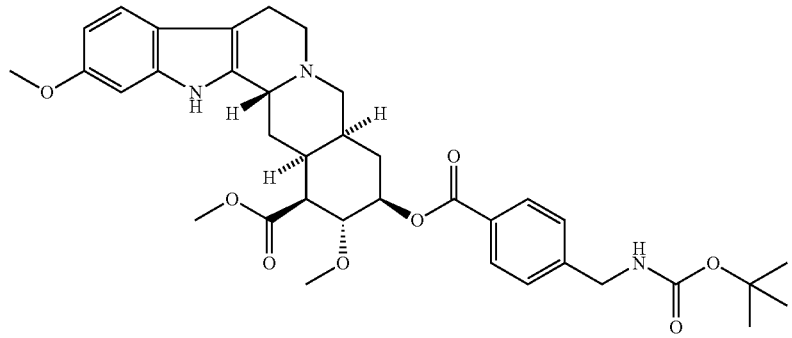 [SMILES: COC(=O)[C@H]1[C@H]2C[C@@H]3c4[nH]c5cc(OC)ccc5c4CCN3C[C@H]2C[C@@H](OC(=O)c2ccc(CNC(=O)OC(C)(C)C)cc2)[C@@H]1OC]

Under N$_2$ atmosphere, 100 mg of methyl (1R,15S,17R, 18R,19S,20S)-17-hydroxy-6,18-dimethoxy-3,13-diazapentacyclo[11.8.0.0$^{2,10}$.0$^{4,9}$.0$^{15,20}$]henicosa-2(10),4,6,8-tetraene-19-carboxylate (CAS 2901-66-8) (0.24 mmol, 1.0 eq.), 182 mg of N-tert-butoxycarbonyl-4-aminomethyl-benzoic acid (0.72 mmol, 3.0 eq.), 149 mg of DCC (0.72 mmol, 3.0 eq.) and 11 mg of 4-PPY (0.07 mmol, 0.3 eq.) are dissolved in 10 mL of DCM. After agitation at 15° C. for 17 hours, the reaction mixture is filtered and the filtrate is concentrated under reduced pressure. The residue is purified by preparative HPLC (eluent: water with 0.05% ammonia and acetonitrile; gradient) to give 140 mg of the desired product as off-white solid.

$^1$H NMR (400 MHz, DMSO-d$_6$) δ ppm: 10.54 (s, 1H), 8.02 (d, J=8.2 Hz, 2H), 7.53 (t, J=6.0 Hz, 1H), 7.41 (d, J=8.4 Hz, 2H), 7.23 (d, J=8.4 Hz, 1H), 6.81 (d, J=2.0 Hz, 1H), 6.62 (dd, J$_1$=8.4 Hz, J$_2$=2.0 Hz, 1H), 4.96 (m, 1H), 4.35 (m, 1H), 4.22 (d, J=6.0 Hz, 2H), 3.89 (dd, J$_1$≈J$_2$=10.4 Hz, 1H), 3.80 (s, 3H), 3.76 (s, 3H), 3.39 (s, 3H), 3.10-1.75 (m, 13H), 1.40 (s, 9H).

MS m/z (+ESI): 648.3 [M+H]$^+$

Example 4

(a) Preparation of methyl (1R,15S,17R,18R,19S, 20S)-17-{[4-(aminomethyl)phenyl]carbonyloxy}-6, 18-dimethoxy-3,13-diazapentacyclo[11.8.0.0$^{2,10}$. 0$^{4,9}$.0$^{15,20}$]henicosa-2(10),4,6,8-tetraene-19-carboxylate

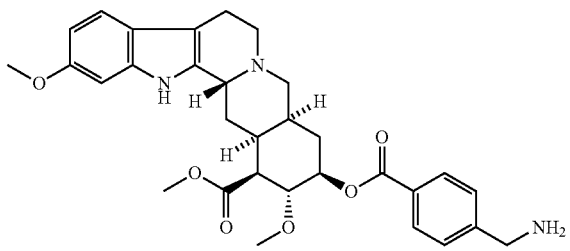 [SMILES: COC(=O)[C@H]1[C@H]2C[C@@H]3c4[nH]c5cc(OC)ccc5c4CCN3C[C@H]2C[C@@H](OC(=O)c2ccc(CN)cc2)[C@@H]1OC]

Under N$_2$ atmosphere, 800 mg of methyl (1R,15S,17R, 18R,19S,20S)-17-{[4-({[(tert-butoxy)carbonyl]amino}methyl)phenyl]carbonyloxy}-6,18-dimethoxy-3,13-diazapentacyclo[11.8.0.0$^{2,10}$.0$^{4,9}$.0$^{15,20}$]henicosa-2(10),4,6, 8-tetraene-19-carboxylate (0.98 mmol, 1.0 eq.) are dissolved in 10 mL of DCM. Then 40 mL of a 2M hydrochloride solution in ethyl acetate (80 mmol, 81.6 eq.) are added. After agitation at 15° C. for 2 hours, the reaction mixture is concentrated under reduced pressure. The residue is purified by preparative HPLC (eluent: water with 0.05% ammonia and acetonitrile; gradient) to give 380 mg of the desired product as white solid.

$^1$H NMR (400 MHz, DMSO-d$_6$) δ ppm: 10.53 (s, 1H), 8.00 (d, J=8.4 Hz, 2H), 7.52 (d, J=8.4 Hz, 2H), 7.23 (d, J=8.8 Hz, 1H), 6.81 (d, J=2.0 Hz, 1H), 6.62 (dd, J$_1$=2.0 Hz and J$_2$=8.4 Hz, 1H), 4.95 (m, 1H), 4.35 (m, 1H), 3.88 (dd, J$_1$≈J$_2$=10.0 Hz, 1H), 3.81 (s, 2H), 3.80 (s, 3H), 3.76 (s, 3H), 3.40 (s, 3H), 3.10-1.75 (m, 13H).

MS m/z (+ESI): 548.3 [M+H]$^+$ (b) Preparation of methyl (1R,15S,17R,18R,19S, 20S)-17-[(4-{[(ethoxycarbonyl)amino] methyl}phenyl)carbonyloxy]-6,18-dimethoxy-3,13-diazapentacyclo[11.8.0.0$^{2,10}$.0$^{4,9}$.0$^{15,20}$]henicosa-2 (10),4,6,8-tetraene-19-carboxylate

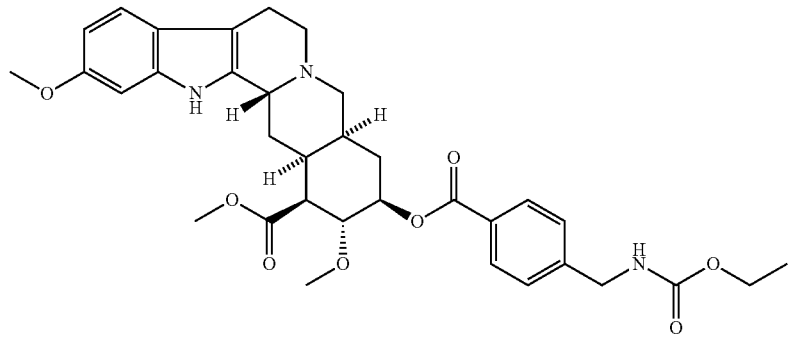 [SMILES: CCOC(=O)NCc1ccc(C(=O)O[C@@H]2C[C@@H]3CN4CCc5c([nH]c6cc(OC)ccc56)[C@H]4C[C@@H]3[C@H](C(=O)OC)[C@H]2OC)cc1]

Under N$_2$ atmosphere, 100 mg of methyl (1R,15S,17R, 18R,19S,20S)-17-{[4-(aminomethyl)phenyl]carbonyloxy}- 6,18-dimethoxy-3,13-diazapentacyclo[11.8.0.0$^{2,10}$.0$^{4,9}$. 0$^{15,20}$]henicosa-2(10),4,6,8-tetraene-19-carboxylate (0.18 mmol, 1.0 eq.) are dissolved in 6 mL of pyridine. Then 99 mg of ethyl chloroformate (1.83 mmol, 5.0 eq.) are added. After agitation at 15° C. for 1 hour, the reaction mixture is concentrated under reduced pressure. The residue is purified by preparative HPLC (eluent: water with 0.05% formic acid and acetonitrile; gradient) to give 62 mg of the desired product as yellow solid (formic acid salt).

$^1$H NMR (400 MHz, DMSO-d$_6$) δ ppm: 10.54 (s, 1H), 8.02 (d, J=8.4 Hz, 2H), 7.77 (t, J=6.0 Hz, 1H), 7.43 (d, J=8.4 Hz, 2H), 7.23 (d, J=8.8 Hz, 1H), 6.81 (d, J=2.0 Hz, 1H), 6.62 (dd, J$_1$=8.8 Hz, J$_2$=2.0 Hz, 1H), 4.95 (m, 1H), 4.37 (s, 1H), 4.28 (d, J=6.0 Hz, 2H), 4.03 (q, J=7.2 Hz, 2H), 3.90 (m, 1H), 3.78 (s, 3H), 3.76 (s, 3H), 3.40 (s, 3H), 3.10-1.75 (m, 13H), 1.19 (t, J=7.2 Hz, 3H).

MS m/z (+ESI): 620.3 [M+H]$^+$

Example 5

Preparation of methyl (1R,15S,17R,18R,19S,20S)- 17-{[4-(2-ethoxy-2-oxoethyl)phenyl]carbonyloxy}- 6,18-dimethoxy-3,13-diazapentacyclo[11.8. 0.0$^{2,10}$.0$^{4,9}$.0$^{15,20}$]henicosa-2(10),4,6,8-tetraene-19- carboxylate

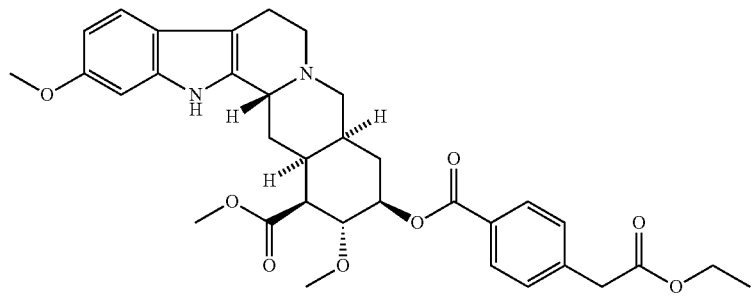 [SMILES: CCOC(=O)Cc1ccc(C(=O)O[C@@H]2C[C@@H]3CN4CCc5c([nH]c6cc(OC)ccc56)[C@H]4C[C@@H]3[C@H](C(=O)OC)[C@H]2OC)cc1]

A solution of 200 mg of (1R,15S,17R,18R,19S,20S)-17- hydroxy-6,18-dimethoxy-3,13-diazapentacyclo[11. 8.0.0$^{2,10}$.0$^{4,9}$.0$^{15,20}$]henicosa-2(10),4,6,8-tetraene-19-car- boxylate (CAS 2901-66-8) (0.48 mmol, 1.0 eq.), 200 mg of 4-carboxy-benzeneacetic acid ethyl ester (CAS 57269-65-5) (0.97 mmol, 2.0 eq.), 18 mg of DMAP (0.14 mmol, 0.3 eq.) and 149 mg of DCC (0.72 mmol, 1.5 eq.) in 20 mL of DCM is stirred at room temperature for 16 hours. Then the reaction mixture is washed with 20 mL of water, dried over Na$_2$SO$_4$, filtered and evaporated under reduced pressure. The residue is purified by preparative HPLC (eluent: water with 0.1% TFA and acetonitrile; gradient) to give 97 mg of the desired product as light yellow solid (TFA salt).

$^1$H NMR (400 MHz, DMSO-d$_6$+D$_2$O) δ ppm: 8.00 (d, J=8.4 Hz, 2H), 7.46 (d, J=8.4 Hz, 2H), 7.37 (d, J=8.8 Hz, 1H), 6.91 (s, 1H), 6.71 (dd, J=8.4 Hz, J$_2$=2.4 Hz, 1H), 5.07 (m, 1H), 4.94 (m, 1H), 4.09 (q, J=7.2 Hz, 2H), 3.89 (m, 1H), 3.80 (s, 3H), 3.76 (s, 3H), 3.71 (s, 2H), 3.39 (s, 3H), 3.62-1.89 (m, 14H), 1.18 (t, J=7.2 Hz, 3H).

MS m/z (+ESI): 605.3 [M+H]$^+$

Example 6

(a) Preparation of 4-nitrophenyl[pyridine-4-yl]methyl]carbonate

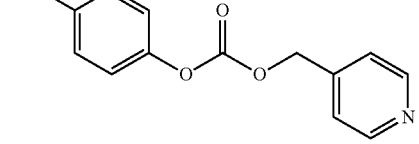

To a solution of 30 mg of 4-hydroxymethylpyridine (0.27 mmol, 1.0 eq.) and 67 mg of 4-nitrophenylchloroformate (0.33 mmol, 1.2 eq.) in 5 mL of DCM are added 56 mg of triethylamine (0.55 mmol, 2 eq.) at 0° C. After agitation at 20° C. for 2 hours, the reaction mixture is evaporated under reduced pressure. The residue is purified by silica gel column chromatography (eluent: petroleum ether/ethyl acetate=1/2 v/v) affording 35 mg of the desired product as white solid.

MS m/z (+ESI): 275.3 [M+H]⁺

(b) Preparation of methyl (1R,15S,17R,18R,19S,20S)-17-[(3,5-dimethoxy-4-{[(pyridin-4-ylmethoxy)carbonyl]oxy}phenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate

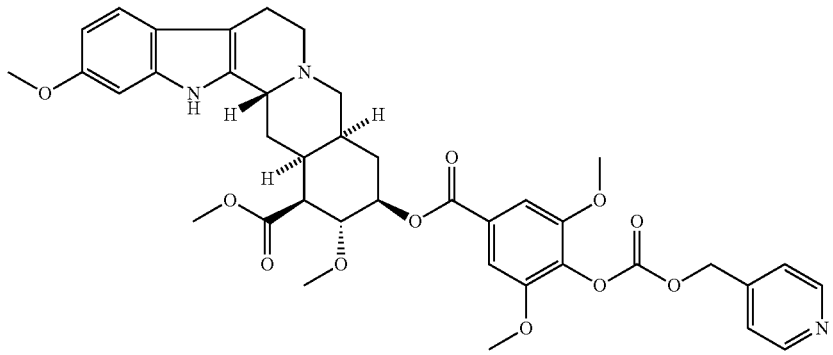 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3ccncc3)c(OC)c2)[C@@H]1OC]

To a solution of 30 mg of 4-nitrophenyl[pyridine-4-yl]methyl]carbonate (CAS 32919-24-7) (0.11 mmol, 1.0 eq.) and 65 mg of methyl (1R,15S,17R,18R,19S,20S)-17-[(4-hydroxy-3,5-dimethoxyphenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate (CAS 21432-74-6) (0.11 mmol, 1.0 eq.) in 5 mL of DMF are added 17 mg of K$_2$CO$_3$ (0.12 mmol, 1.1 eq.). After agitation at 20° C. for 20 hours, the reaction mixture is diluted with 50 mL of ethyl acetate, washed three times with 20 mL of water, dried over Na$_2$SO$_4$, filtered and concentrated under reduced pressure. The residue is purified by preparative HPLC (eluent: water with 0.02% ammonia and acetonitrile; gradient) to give 30 mg of the desired product as white solid.

$^1$H NMR (400 MHz, DMSO-d$_6$) δ ppm: 10.55 (s, 1H), 8.65 (d, J=5.6 Hz, 2H), 7.44 (s, 2H), 7.41 (d, J=5.6 Hz, 2H), 7.23 (d, J=8.4 Hz, 1H), 6.81 (d, J=2.0 Hz, 1H), 6.62 (dd, J$_1$=2.0 Hz and J$_2$=8.4 Hz, 1H), 5.38 (s, 2H), 4.99-4.97 (m, 1H), 4.36 (m, 1H), 3.97 (dd, J$_1$=J$_2$=10.0 Hz, 1H), 3.95 (s, 6H), 3.81 (s, 3H), 3.76 (s, 3H), 3.42 (s, 3H), 3.06-1.81 (m, 13H).

MS m/z (+ESI): 730.3 [M+H]⁺, 365.9 [M+2H]²⁺

Example 7

Preparation of methyl (1R,15S,17R,18R,19S,20S)-17-[(3,5-dimethoxy-4-{[(pyridin-3-ylmethoxy)carbonyl]oxy}phenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate

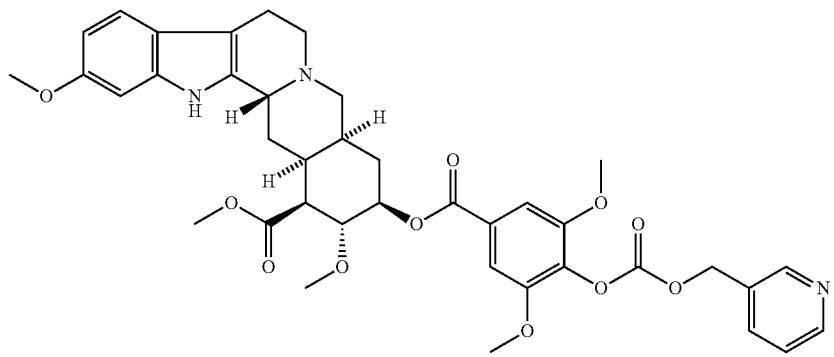 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3cccnc3)c(OC)c2)[C@@H]1OC]

The product is obtained according to Example 6 from 4-nitrophenyl[pyridine-3-yl]methyl]carbonate (CAS 32939-32-5) and methyl (1R,15S,17R,18R,19S,20S)-17-[(4-hydroxy-3,5-dimethoxyphenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate (CAS 21432-74-6).

$^1$H NMR (400 MHz, DMSO-d$_6$) δ ppm: 10.55 (s, 1H), 8.67 (d, J=2.0 Hz, 1H), 8.62 (dd, J$_1$=1.6 Hz and J$_2$=4.8 Hz, 1H), 7.90-7.86 (m, 1H), 7.52-7.48 (m, 1H), 7.42 (s, 2H), 7.23 (d, J=8.8 Hz, 1H), 6.81 (d, J=2.4 Hz, 1H), 6.62 (dd, J$_1$=2.4 Hz and J$_2$=8.8 Hz, 1H), 5.36 (s, 2H), 5.00-4.80 (m, 1H), 4.40-4.20 (m, 1H), 4.03-3.94 (m, 1H), 3.87 (s, 6H), 3.81 (s, 3H), 3.76 (s, 3H), 3.42 (s, 3H), 3.06-1.61 (m, 13H).
MS m/z (+ESI): 730.2 [M+H]$^+$, 365.8 [M+2H]$^{2+}$ Example 8

Preparation of methyl (1R,15S,17R,18R,19S,20S)-17-{[4-({[(3,5-dimethoxyphenyl)methoxy]carbonyl}oxy)-3,5-dimethoxyphenyl]carbonyloxy}-6,18-dimethoxy-3,13-diazapentacyclo[11.8.0.0$^{2,10}$.0$^{4,9}$.0$^{15,20}$]henicosa-2(10),4,6,8-tetraene-19-carboxylate

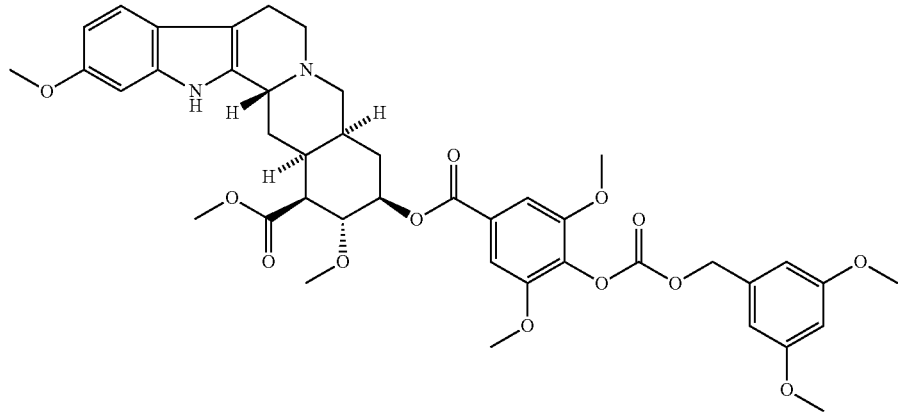

The product is obtained according to Example 6 from 4-nitrophenyl-(3,5-dimethoxybenzyl)carbonate (CAS 6453-62-9) and methyl (1R,15S,17R,18R,19S,20S)-17-[(4-hydroxy-3,5-dimethoxyphenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate (CAS 21432-74-6).

$^1$H NMR (400 MHz, DMSO-d$_6$) δ ppm: 10.56 (s, 1H), 7.43 (s, 2H), 7.23 (d, J=8.4 hz, 1H), 6.81 (d, J=2.0 Hz, 1H), 6.62 (dd, J$_1$=2.0 Hz and J$_2$=8.4 Hz, 1H), 6.59 (d, J=2.0 Hz, 2H), 6.53 (d, J=2.0 Hz, 1H), 5.24 (s, 2H), 4.99-4.96 (m, 1H), 4.36 (m, 1H), 4.00-3.94 (m, 1H), 3.89 (s, 6H), 3.89 (s, 3H), 3.81 (s, 6H), 3.42 (s, 3H), 3.05-1.80 (m, 13H)
MS m/z (+ESI): 789.3 [M+H]$^+$ Example 9

Preparation of methyl (1R,15S,17R,18R,19S,20S)-17-{[4-({[(4-chlorophenyl)methoxy]carbonyl}oxy)-3,5-dimethoxyphenyl]carbonyloxy}-6,18-dimethoxy-3,13-diazapentacyclo[11.8.0.0$^{2,10}$.0$^{4,9}$.0$^{15,20}$]henicosa-2(10),4,6,8-tetraene-19-carboxylate

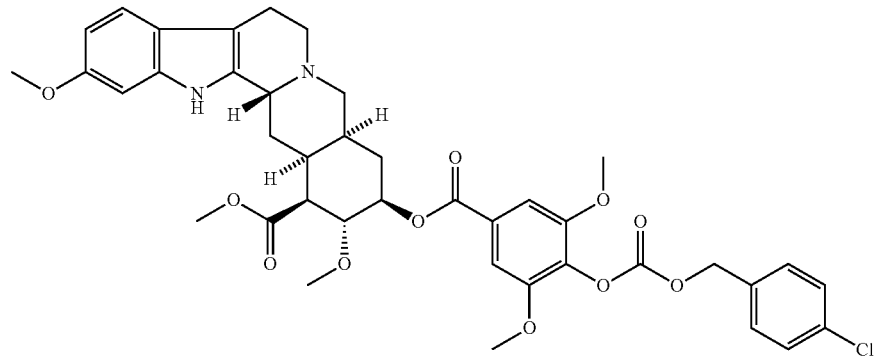 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3ccc(Cl)cc3)c(OC)c2)[C@@H]1OC]

The product is obtained according to Example 6 from 4-nitrophenyl-(4-chlorobenzyl)carbonate (CAS 97534-88-8) and methyl (1R,15S,17R,18R,19S,20S)-17-[(4-hydroxy-3,5-dimethoxyphenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate (CAS 21432-74-6).

$^1$H NMR (400 MHz, DMSO-d$_6$) δ ppm: 10.54 (s, 1H), 7.53 (d, J=8.4 Hz, 2H), 7.47 (d, J=8.4 Hz, 2H), 7.42 (s, 2H), 7.23 (d, J=8.4 Hz, 1H), 6.81 (d, J=2.0 Hz, 1H), 6.62 (dd, J$_1$=2.0 Hz and J$_2$=8.4 Hz, 1H), 5.31 (s, 2H), 5.00-4.80 (m, 1H), 4.37 (m, 1H), 4.00-3.94 (m, 1H), 3.89 (s, 6H), 3.80 (s, 3H), 3.76 (s, 3H), 3.42 (s, 3H), 3.06-1.80 (m, 13H)

MS m/z (+ESI): 763.2 [M+H]$^+$

Example 10

Preparation of methyl (1R,15S,17R,18R,19S,20S)-17-{[4-({[(3,5-dichlorophenyl)methoxy]carbonyl}oxy)-3,5-dimethoxyphenyl]carbonyloxy}-6,18-dimethoxy-3,13-diazapentacyclo[11.8.0.0$^{2,10}$.0$^{4,9}$.0$^{15,20}$]henicosa-2(10),4,6,8-tetraene-19-carboxylate

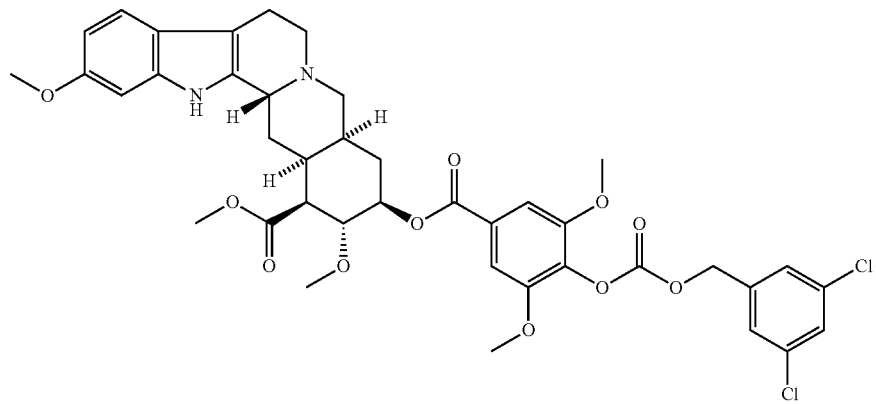 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3cc(Cl)cc(Cl)c3)c(OC)c2)[C@@H]1OC]

The product is obtained according to Example 6 from 4-nitrophenyl-(3,5-dichlorobenzyl)carbonate (prepared according to the preparation of 4-nitrophenyl[pyridine-4-yl]methyl]carbonate) and methyl (1R,15S,17R,18R,19S,20S)-17-[(4-hydroxy-3,5-dimethoxyphenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate (CAS 21432-74-6).

$^1$H NMR (400 MHz, DMSO-d$_6$) δ ppm: 10.54 (s, 1H), 7.67 (d, J$_1$=J$_2$=2.0 Hz, 1H), 7.49 (d, J=2.0 Hz, 2H), 7.44 (s, 2H), 7.23 (d, J=8.4 Hz, 1H), 6.81 (d, J=2.4 Hz, 1H), 6.62 (dd, J$_1$=2.0 Hz and J$_2$=8.4 Hz, 1H), 5.34 (s, 2H), 5.00-4.90 (m, 1H), 4.36 (m, 1H), 4.00-3.94 (m, 1H), 3.90 (s, 6H), 3.81 (s, 3H), 3.76 (s, 3H), 3.43 (s, 3H), 3.06-1.80 (m, 13H).

MS m/z (+ESI): 797.2 [M+H]$^+$

Example 11

Preparation of methyl (1R,15S,17R,18R,19S,20S)-17-{[3,5-dimethoxy-4-({[(4-methoxyphenyl)methoxy]carbonyl}oxy)phenyl]carbonyloxy}-6,18-dimethoxy-3,13-diazapentacyclo[11.8.0.0$^{2,10}$.0$^{4,9}$.0$^{15,20}$]henicosa-2(10),4,6,8-tetraene-19-carboxylate

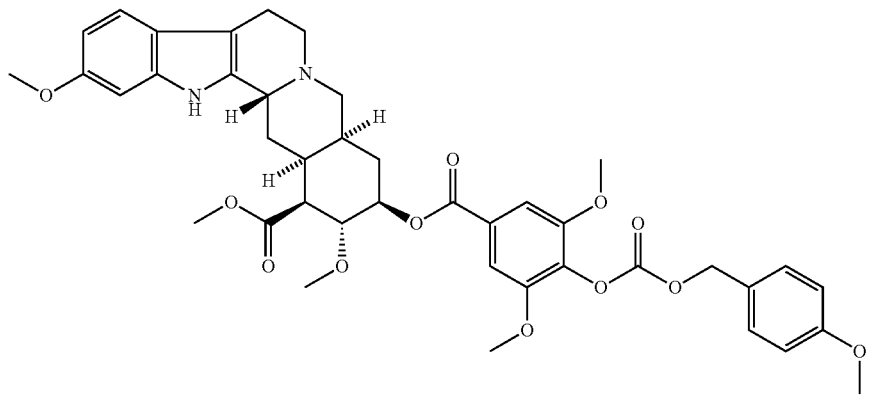

The product is obtained according to Example 6 from 4-nitrophenyl-(4-methoxybenzyl)carbonate (CAS 25506-37-0) and methyl (1R,15S,17R,18R,19S,20S)-17-[(4-hydroxy-3,5-dimethoxyphenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate (CAS 21432-74-6).

$^{1}$H NMR (400 MHz, DMSO-d$_6$) δ ppm: 10.54 (s, 1H), 7.42 (s, 2H), 7.39 (d, J=8.4 Hz, 2H), 7.23 (d, J=8.8 Hz, 1H), 7.00 (d, J=8.8 Hz, 2H), 6.81 (d, J=2.0 Hz, 1H), 6.62 (dd, J$_1$=2.0 Hz and J$_2$=8.8 Hz, 1H), 5.22 (s, 2H), 4.99-4.93 (m, 1H), 4.36 (m, 1H), 3.98-3.96 9m, 1H), 3.88 (s, 6H), 3.81 (s, 3H), 3.79 (s, 3H), 3.76 (s, 3H), 3.42 (s, 3H), 3.05-1.80 (m, 13H).

MS m/z (+ESI): 759.3 [M+H]$^{+}$

Example 12

(a) Preparation of tert-butyl (1S,2S,4R,18S,20R,23R)-23-methoxy-22-oxo-21-oxa-6,16-diazahexacyclo[18.2.1.0$^{2,18}$.0$^{4,16}$.0$^{5,13}$.0$^{7,12}$]tricosa-5(13),7,9,11-tetraen-9-yl carbonate

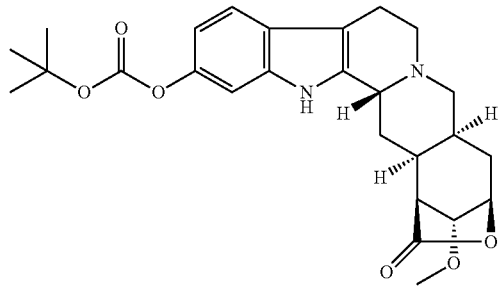 [SMILES: CO[C@@H]1[C@H]2C(=O)O[C@@H]1C[C@@H]1CN3CCc4c([nH]c5cc(OC(=O)OC(C)(C)C)ccc45)[C@H]3C[C@@H]12]

To a solution of 1.00 g (2.71 mmol, 1.0 eq.) of (1S,2S,4R,18S,20R,23R)-9-hydroxy-23-methoxy-21-oxa-6,16-diazahexacyclo[18.2.1.0$^{2,18}$.0$^{4,16}$.0$^{5,13}$.0$^{7,12}$]tricosa-5(13),7,9,11-tetraen-22-one (CAS 866412-74-0) (prepared according to G. Varchi, A. Battaglia, C. Samori, E. Baldelli, B. Danieli, G. Fontana, A. Guerrini and E. Bombardelli, *J. Nat. Prod.* 2005, 68, 1629-1631) in 10 mL of DMF are added 67 mg of DMAP (0.54 mmol, 0.2 eq.) and 711 mg of di-tert-butyl dicarbonate (3.26 mmol, 1.2 eq.). After agitation 35° C. for 1 hour, the reaction mixture is concentrated under reduced pressure. The residue is washed with 2 mL of methanol and dried under vacuum to afford 1.00 g of the desired product as white solid.

$^{1}$H NMR (400 MHz, DMSO-d$_6$) δ ppm: 10.94 (s, 1H), 7.33 (d, J=8.4 Hz, 1H), 7.06 (d, J=2.0 Hz, 1H), 6.75 (dd, J$_1$=2.0 Hz and J$_2$=8.4 Hz, 1H), 4.81-4.78 (m, 1H), 4.16-4.13 (m, 1H), 3.52-3.48 (m, 1H), 3.40-1.50 (m, 25H)

MS m/z (+ESI): 469 [M+H]$^{+}$ (b) Preparation of methyl (1R,15S,17R,18R,19S,20S)-6-{[(tert-butoxy)carbonyl]oxy}-17-hydroxy-18-methoxy-3,13-diazapentacyclo[11.8.0.0$^{2,10}$.0$^{4,9}$.0$^{15,20}$]henicosa-2(10),4,6,8-tetraene-19-carboxylate

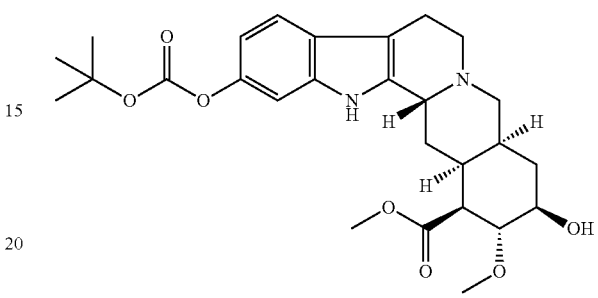

To a solution of 550 mg of tert-butyl (1S,2S,4R,18S,20R,23R)-23-methoxy-22-oxo-21-oxa-6,16-diazahexacyclo [18.2.1.0$^{2,18}$.0$^{4,16}$.0$^{5,13}$.0$^{7,12}$]tricosa-5(13),7,9,11-tetraen-9-yl carbonate (1.17 mmol, 1.0 eq.) in 60 mL of methanol are added 32 mg of sodium methoxide (0.59 mmol, 0.5 eq.). After refluxing at 65° C. for 1 hour, the reaction mixture is concentrated under reduced pressure. The residue is dissolved in 30 mL of DCM and washed with 10 mL of water. The organic phase is dried with MgSO$_4$, filtered and concentrated under reduced pressure to afford 520 mg of the crude desired product as light yellow solid which is used in the next step without further purification.

$^{1}$H NMR (400 MHz, DMSO-d$_6$) δ ppm: 10.80 (s, 1H), 7.33 (d, J=8.4 Hz, 1H), 7.06 (d, J=2.4 Hz, 1H), 6.75 (dd, J$_1$=2.4 Hz and J$_2$=8.4 Hz, 1H), 4.85-4.83 (m, 1H), 4.37-4.34 (m, 1H), 3.75 (s, 3H), 3.47 (s, 3H), 3.38-1.50 (m, 23H).

MS m/z (+ESI): 501 [M+H]$^{+}$ (c) Preparation of methyl (1R,15S,17R,18R,19S,20S)-6-{[(tert-butoxy)carbonyl]oxy}-17-({4-[(ethoxycarbonyl)oxy]-3,5-dimethoxyphenyl}carbonyloxy)-18-methoxy-3,13-diazapentacyclo[11.8.0.0$^{2,10}$.0$^{4,9}$.0$^{15,20}$]henicosa-2(10),4,6,8-tetraene-19-carboxylate

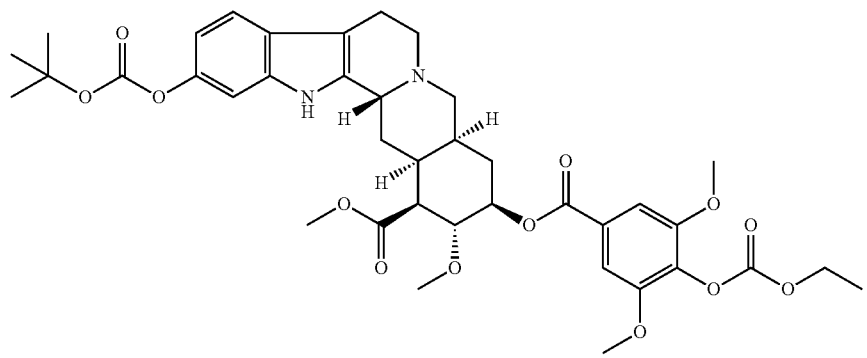 [SMILES: CCOC(=O)Oc1c(OC)cc(C(=O)O[C@@H]2C[C@@H]3CN4CCc5c([nH]c6cc(OC(=O)OC(C)(C)C)ccc56)[C@H]4C[C@@H]3[C@H](C(=O)OC)[C@H]2OC)cc1OC]

A mixture containing 450 mg of methyl (1R,15S,17R,18R,19S,20S)-6-{[(tert-butoxy)carbonyl]oxy}-17-hydroxy-18-methoxy-3,13-diazapentacyclo[11.8.0.0$^{2,10}$.0$^{4,9}$.0$^{15,20}$]henicosa-2(10),4,6,8-tetraene-19-carboxylate (0.90 mmol, 1.0 eq.), 292 mg of 4-[(ethoxycarbonyl)oxy]-3,5-dimethoxy-benzoic acid (CAS 18780-67-1) (1.08 mmol, 1.2 eq.), 278 mg of DCC (1.35 mmol, 1.5 eq.), 22 mg of DMAP (0.18 mmol, 0.2 eq.) and 10 mL of DCM is stirred at room temperature for 20 hours. Then the reaction mixture is concentrated under the reduced pressure. The residue is purified by silica gel column chromatography (eluent: DCM/methanol=150/1-100/1, v/v). The obtained crude product is further purified by preparative HPLC (eluent: water with 0.02% ammonia and acetonitrile; gradient) to afford 180 mg of the desired product as white solid.

$^1$H NMR (400 MHz, DMSO-d$_6$) δ ppm: 10.87 (s, 1H), 7.42 (s, 2H), 7.34 (d, J=8.4 Hz, 1H), 7.08 (d, J=2.0 Hz, 1H), 6.76 (dd, J$_1$=2.0 Hz and J$_2$=8.4 Hz, 1H), 5.00-4.95 (m, 1H), 4.40 (m, 1H), 4.26 (q, J=7.2 Hz, 2H), 4.01-3.95 (m, 1H), 3.90 (s, 6H), 3.80 (s, 3H), 3.42 (s, 3H), 3.08-1.83 (m, 13H), 1.50 (s, 9H), 1.35 (t, J=7.2 Hz, 3H)

MS m/z (+ESI): 753.3 [M+H]$^+$

Example 13

Preparation of methyl (1R,15S,17R,18R,19S,20S)-17-({4-[(ethoxycarbonyl)oxy]-3,5-dimethoxyphenyl}carbonyloxy)-6-hydroxy-18-methoxy-3,13-diazapentacyclo[11.8.0.0$^{2,10}$.0$^{4,9}$.0$^{15,20}$]henicosa-2(10),4,6,8-tetraene-19-carboxylate

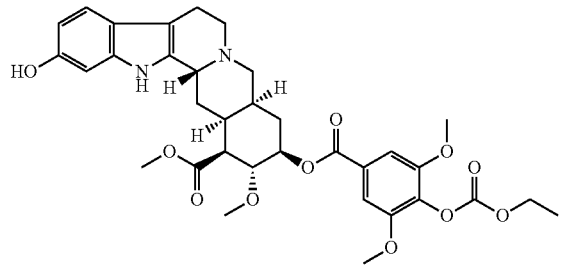 [SMILES: CCOC(=O)Oc1c(OC)cc(C(=O)O[C@@H]2C[C@@H]3CN4CCc5c([nH]c6cc(O)ccc56)[C@H]4C[C@@H]3[C@H](C(=O)OC)[C@H]2OC)cc1OC]

300 mg of methyl (1R,15S,17R,18R,19S,20S)-6-{[(tert-butoxy)carbonyl]oxy}-17-({4-[(ethoxycarbonyl)oxy]-3,5-dimethoxyphenyl}carbonyloxy)-18-methoxy-3,13-diazapentacyclo [11.8.0.0$^{2,10}$.0$^{4,9}$.0$^{15,20}$]henicosa-2(10),4,6,8-tetraene-19-carboxylate (0.40 mmol, 1.0 eq.) are dissolved in 10 mL of acetonitrile. Then 1.0 mL of concentrated aqueous hydrochloric acid is added. After agitation at 35° C. for 1 hour, the reaction mixture is evaporated under reduced pressure. The residue is purified by preparative HPLC (eluent: water with 0.02% ammonia and acetonitrile; gradient) to give 100 mg of the desired product as white solid.

$^1$H NMR (400 MHz, DMSO-d$_6$) δ ppm: 10.36 (s, 1H), 8.79 (s, 1H), 7.42 (s, 2H), 7.12 (d, J=8.4 Hz, 1H), 6.68 (d, J=2.0 Hz, 1H), 6.47 (dd, J$_1$=2.0 Hz and J$_2$=8.4 Hz, 1H), 4.98-4.96 (m, 1H), 4.35 (m, 1H), 4.26 (q, J=7.2 Hz, 2H), 3.96 (dd, J$_1$≈J$_2$=10.4 Hz, 1H), 3.90 (s, 6H), 3.80 (s, 3H), 3.42 (s, 3H), 3.04-1.76 (m, 13H), 1.30 (t, J=7.2 Hz, 3H).

MS m/z (+ESI): 563.3 [M+H]$^+$

Example 14

Preparation of methyl (1R,15S,17R,18R,19S,20S)-6-(acetyloxy)-17-({4-[(ethoxycarbonyl)oxy]-3,5-dimethoxyphenyl}carbonyloxy)-18-methoxy-3,13-diazapentacyclo[11.8.0.0$^{2,10}$.0$^{4,9}$.0$^{15,20}$]henicosa-2(10),4,6,8-tetraene-19-carboxylate

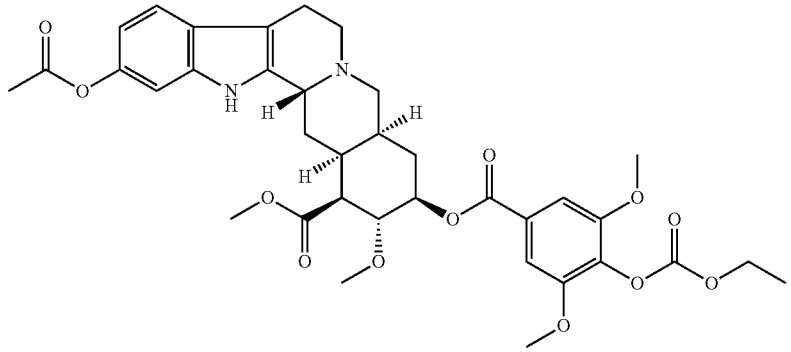 [SMILES: CCOC(=O)Oc1c(OC)cc(C(=O)O[C@@H]2C[C@@H]3CN4CCc5c([nH]c6cc(OC(C)=O)ccc56)[C@H]4C[C@@H]3[C@H](C(=O)OC)[C@H]2OC)cc1OC]

60 mg of methyl (1R,15S,17R,18R,19S,20S)-17-({4-[(ethoxycarbonyl)oxy]-3,5-dimethoxyphenyl}carbonyloxy)-6-hydroxy-18-methoxy-3,13-diazapentacyclo[11.8.0.0$^{2,10}$.0$^{4,9}$.0$^{15,20}$]henicosa-2(10),4,6,8-tetraene-19-carboxylate (0.09 mmol, 1.0 eq.) and 6 mg of DMAP (0.05 mmol, 0.5 eq.) are dissolved in 5 mL of DCM. Then 14 mg of acetic anhydride (0.14 mmol, 1.5 eq.) are added. After agitation at 15° C. for 1 hour, the reaction mixture is concentrated under reduced pressure. The residue is purified by preparative HPLC (eluent: water with 0.02% ammonia and acetonitrile; gradient) to give 50 mg of the desired product as white solid.

$^1$H NMR (400 MHz, DMSO-d$_6$) δ ppm: 10.87 (s, 1H), 7.42 (s, 2H), 7.34 (d, J=8.4 Hz, 1H), 7.03 (d, J=2.0 Hz, 1H), 6.71 (dd, J$_1$=2.0 Hz and J$_2$=8.4 Hz, 1H), 5.00-4.93 (m, 1H), 4.40 (m, 1H), 4.26 (q, J=7.2 Hz, 2H), 4.00-3.95 (m, 1H), 3.90 (s, 6H), 3.79 (s, 3H), 3.42 (s, 3H), 3.08-1.77 (m, 16H), 1.30 (t, J=7.2 Hz, 3H)

MS m/z (+ESI): 695.2 [M+H]$^+$

Example 15

Preparation of methyl (1R,15S,17R,18R,19S,20S)-6-(benzoyloxy)-17-({4-[(ethoxycarbonyl)oxy]-3,5-dimethoxyphenyl}carbonyloxy)-18-methoxy-3,13-diazapentacyclo[11.8.0.0$^{2,10}$.0$^{4,9}$.0$^{15,20}$]henicosa-2(10),4,6,8-tetraene-19-carboxylate

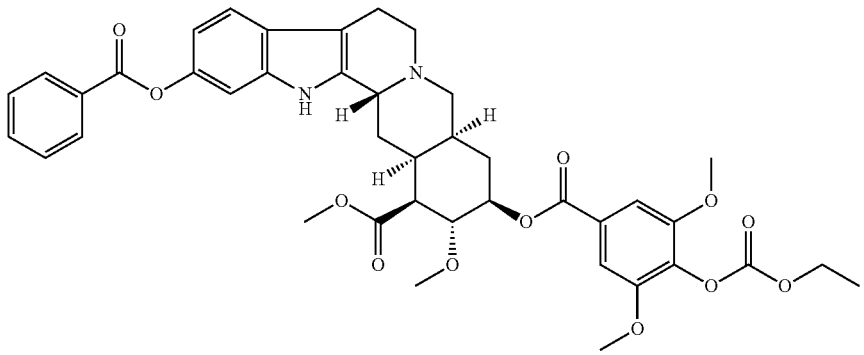 [SMILES: CCOC(=O)Oc1c(OC)cc(C(=O)O[C@@H]2C[C@@H]3CN4CCc5c([nH]c6cc(OC(=O)c7ccccc7)ccc56)[C@H]4C[C@@H]3[C@H](C(=O)OC)[C@H]2OC)cc1OC]

100 mg of methyl (1R,15S,17R,18R,19S,20S)-17-({4-[(ethoxycarbonyl)oxy]-3,5-dimethoxyphenyl}carbonyloxy)-6-hydroxy-18-methoxy-3,13-diazapentacyclo[11.8.0.0$^{2,10}$.0$^{4,9}$.0$^{15,20}$]henicosa-2(10),4,6,8-tetraene-19-carboxylate (0.15 mmol, 1.0 eq.) are dissolved in 2 mL of pyridine. Then 178 uL of benzoyl chloride (1.53 mmol, 10 eq.) and 10 mg of DMAP (0.08 mmol, 0.5 eq.) are added. After agitation at 46° C. for 3 hours, the reaction mixture is concentrated under reduced pressure. The residue is purified by silica gel column chromatography (eluent: DCM/methanol=100/1-40/1, v/v).

The obtained product was further purified by preparative HPLC (eluent: water with 0.02% ammonia and acetonitrile; gradient) to give 45 mg of the desired product as white solid.

$^1$H NMR (400 MHz, DMSO-d$_6$) δ ppm: 10.94 (s, 1H), 8.17 (d, J=7.6 Hz, 2H), 7.76 (dd, J$_1$=J$_2$=7.6 Hz, 1H), 7.63 (dd, J$_1$≈J$_2$=7.6 Hz, 2H), 7.43-7.39 (m, 3H), 7.19 (d, J=2.0 Hz, 1H), 6.87 (dd, J$_1$=2.0 Hz and J$_2$=8.4 Hz, 1H), 5.00-4.80 (m, 1H), 4.42 (m, 1H, H-3), 4.26 (q, J=7.2 Hz, 2H), 4.00-3.95 (m, 1H), 3.90 (s, 6H), 3.79 (s, 3H), 3.42 (s, 3H), 3.09-1.77 (m, 13H), 1.30 (t, J=7.2 Hz, 3H, H-d).

MS m/z (+ESI): 757.2 [M+H]$^+$

Example 16

(a) Preparation of methyl (1R,15S,17R,18R,19S,20S)-6-[(2-{[(tert-butoxy)carbonyl]amino}acetyl)oxy]-17-({4-[(ethoxycarbonyl)oxy]-3,5-dimethoxyphenyl}carbonyloxy)-18-methoxy-3,13-diazapentacyclo[11.8.0.0$^{2,10}$.0$^{4,9}$.0$^{15,20}$]henicosa-2(10),4,6,8-tetraene-19-carboxylate

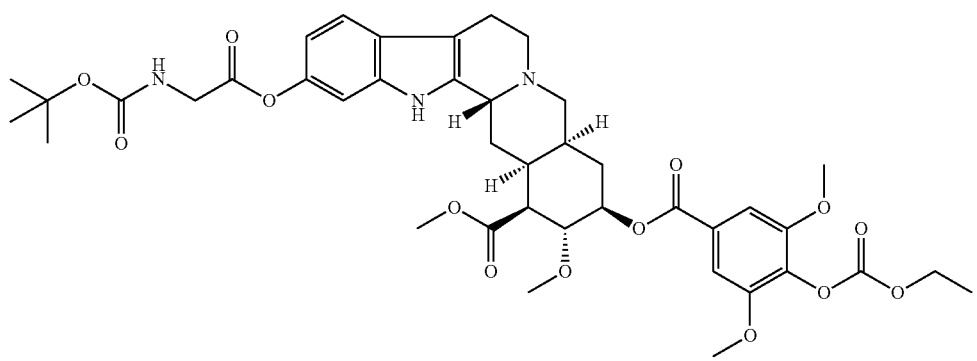 [SMILES: CCOC(=O)Oc1c(OC)cc(C(=O)O[C@@H]2C[C@@H]3CN4CCc5c([nH]c6cc(OC(=O)CNC(=O)OC(C)(C)C)ccc56)[C@H]4C[C@@H]3[C@H](C(=O)OC)[C@H]2OC)cc1OC]

20 mg of methyl (1R,15S,17R,18R,19S,20S)-17-({4-[(ethoxycarbonyl)oxy]-3,5-dimethoxyphenyl}carbonyloxy)-6-hydroxy-18-methoxy-3,13-diazapentacyclo[11.8.0.0$^{2,10}$.0$^{4,9}$.0$^{15,20}$]henicosa-2(10),4,6,8-tetraene-19-carboxylate (0.03 mmol, 10.0 eq.) and 11 mg of N-[(1,1-dimethylethoxy)carbonyl]-glycine (0.06 mmol, 2.0 eq.) are dissolved in 2 mL of DCM. Then two drops of DMF, 26 mg of DCC (0.12 mmol, 4.0 eq.) and 2 mg of DMAP (0.02 mmol, 0.5 eq.) are added. After agitation at room temperature for 1 hour, the reaction mixture is evaporated under reduced pressure. The residue is purified by preparative TLC (eluent: DCM/methanol=15/1, v/v) to give 15 mg of the desired product as white solid.

MS m/z (+ESI): 810.5 [M+H]$^+$ (b) Preparation of methyl (1R,15S,17R,18R,19S,20S)-6-[(2-aminoacetyl)oxy]-17-({4-[(ethoxycarbonyl)oxy]-3,5-dimethoxyphenyl}carbonyloxy)-18-methoxy-3,13-diazapentacyclo[11.8.0.0$^{2,10}$.0$^{4,9}$.0$^{15,20}$]henicosa-2(10),4,6,8-tetraene-19-carboxylate

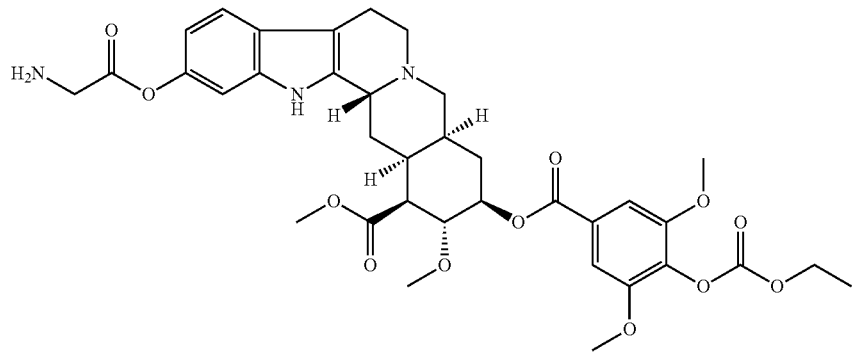 [SMILES: CCOC(=O)Oc1c(OC)cc(C(=O)O[C@@H]2C[C@@H]3CN4CCc5c([nH]c6cc(OC(=O)CN)ccc56)[C@H]4C[C@@H]3[C@H](C(=O)OC)[C@H]2OC)cc1OC]

240 mg of methyl (1R,15S,17R,18R,19S,20S)-6-[(2-{[(tert-butoxy)carbonyl]amino}acetyl)oxy]-17-({4-[(ethoxycarbonyl)oxy]-3,5-dimethoxyphenyl}carbonyloxy)-18-methoxy-3,13-diazapentacyclo[11.8.0.0$^{2,10}$.0$^{4,9}$.0$^{15,20}$]henicosa-2(10),4,6,8-tetraene-19-carboxylate (0.30 mmol, 1.0 eq.) are dissolved in 3 mL of a saturated solution of hydrochloride in ethyl acetate. After agitation at 15° C. for 1 hour, the reaction mixture is evaporated under reduced pressure. The residue is purified by preparative HPLC (eluent: water with 0.1% TFA and acetonitrile; gradient) to afford 135 mg of the desired product as off-white solid (TFA salt).

$^1$H NMR (400 MHz, DMSO-d$_6$+D$_2$O) δ ppm: 11.44 (s, 1H), 7.56 (d, J=8.4 Hz, 1H), 7.40 (s, 2H), 7.22 (d, J=2.0 Hz, 1H), 6.89 (dd, J$_1$=2.0 Hz and J$_2$=8.4 Hz, 1H), 5.17-5.00 (m, 1H), 4.98-4.94 (m, 1H), 4.25 (q, J=7.2 Hz, 2H), 4.11 (s, 2H), 3.96 (dd, J$_1$≈J$_2$=10.0 Hz, 1H), 3.88 (s, 6H), 3.79 (s, 3H), 3.64-1.97 (m, 16H), 1.30 (t, J=7.2 Hz, 3H).

MS m/z (+ESI): 710.3 [M+H]$^+$

Example 17

Preparation of methyl (1R,15S,17R,18R,19S,20S)-6-[(2-acetamidoacetyl)oxy]-17-({4-[(ethoxycarbonyl)oxy]-3,5-dimethoxyphenyl}carbonyloxy)-18-methoxy-3,13-diazapentacyclo[11.8.0.0$^{2,10}$.0$^{4,9}$.0$^{15,20}$]henicosa-2(10),4,6,8-tetraene-19-carboxylate

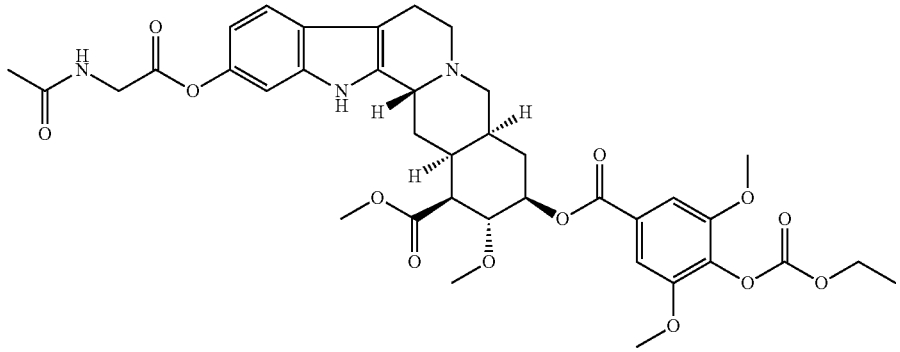 [SMILES: CCOC(=O)Oc1c(OC)cc(C(=O)O[C@@H]2C[C@@H]3CN4CCc5c([nH]c6cc(OC(=O)CNC(C)=O)ccc56)[C@H]4C[C@@H]3[C@H](C(=O)OC)[C@H]2OC)cc1OC]

To a solution of 175 mg of methyl (1R,15S,17R,18R,19S, 20S)-6-[(2-aminoacetyl)oxy]-17-({4-[(ethoxycarbonyl) oxy]-3,5-dimethoxyphenyl}carbonyloxy)-18-methoxy-3, 13-diazapentacyclo[11.8.0.0$^{2,10}$.0$^{4,9}$.0$^{15,20}$]henicosa-2(10), 4,6,8-tetraene-19-carboxylate (0.25 mmol, 1.0 eq.) and 90 mg of DMAP (0.74 mmol, 3.0 eq.) in 5 mL of DCM are added 50 mg of acetic anhydride (0.49 mmol, 2.0 eq.). After agitation at 15° C. for 1 hour, the reaction mixture is evaporated under reduced pressure. The residue is purified by silica gel column chromatography (eluent: DCM/methanol=30/1-15/1, v/v). The obtained product is further purified by preparative HPLC (eluent: water with 0.1% TFA and acetonitrile; gradient) to give 100 mg of the desired product as white solid (TFA salt).

$^1$H NMR (400 MHz, DMSO-d$_6$+D$_2$O) δ ppm: 11.37 (s, 1H), 7.51 (d, J=8.4 Hz, 1H), 7.40 (s, 2H), 7.14 (d, J=2.0 Hz, 1H), 6.82 (dd, J$_1$=2.0 Hz and J$_2$=8.4 Hz, 1H), 5.14 (m, 1H), 5.00-4.93 (m, 1H), 4.25 (q, J=7.2 Hz, 2H), 4.10 (s, 2H), 3.98-3.95 (m, 1H), 3.88 (s, 6H), 3.79 (s, 3H), 3.62-1.85 (m, 19H), 1.30 (t, J=7.2 Hz).

MS m/z (+ESI): 752.5 [M+H]$^+$

Example 18

Preparation of methyl (1R,15S,17R,18R,19S,20S)-17-({4-[(ethoxycarbonyl)oxy]-3,5-dimethoxyphenyl}carbonyloxy)-18-methoxy-6-{[2-(phenylformamido)acetyl]oxy}-3,13-diazapentacyclo[11.8.0.0$^{2,10}$.0$^{4,9}$.0$^{15,20}$]henicosa-2(10),4,6,8-tetraene-19-carboxylate

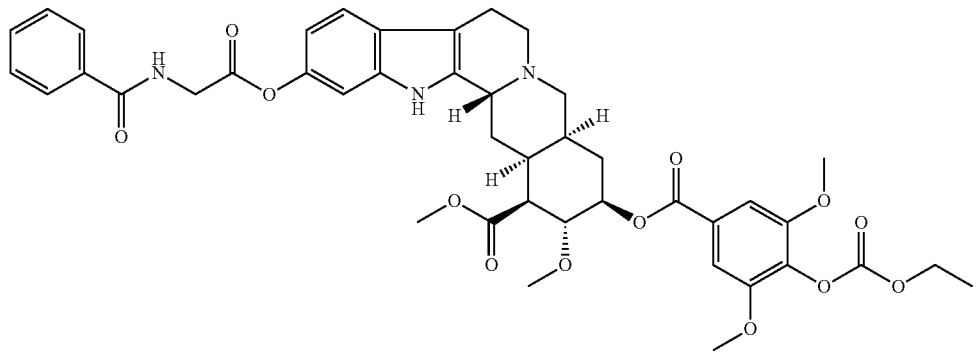 [SMILES: CCOC(=O)Oc1c(OC)cc(C(=O)O[C@@H]2C[C@@H]3CN4CCc5c([nH]c6cc(OC(=O)CNC(=O)c7ccccc7)ccc56)[C@H]4C[C@@H]3[C@H](C(=O)OC)[C@H]2OC)cc1OC]

175 mg of methyl (1R,15S,17R,18R,19S,20S)-6-[(2-aminoacetyl)oxy]-17-({4-[(ethoxycarbonyl)oxy]-3,5-dimethoxyphenyl}carbonyloxy)-18-methoxy-3,13-diazapentacyclo[11.8.0.0$^{2,10}$.0$^{4,9}$.0$^{15,20}$]henicosa-2(10),4,6,8-tetraene-19-carboxylate (0.25 mmol, 1.0 eq.) are dissolved in 5 mL of THF. Then 0.35 mL of triethylamine (2.46 mmol, 10.0 eq.) and 0.3 mL of benzoyl chloride (2.46 mmol, 10.0 eq.) are added. After agitation at 15° C. for 1 hour, the reaction mixture is evaporated under reduced pressure. The residue is purified by silica gel column chromatography (eluent: DCM/methanol=30/1-15/1, v/v). The obtained product is further purified by preparative HPLC (eluent: water with 0.1% TFA and acetonitrile; gradient) to give 100 mg of the desired product as white solid (TFA salt).

$^1$H NMR (400 MHz, DMSO-d$_6$) δ ppm: 11.38 (s, 1H), 7.91 (d, J=7.2 Hz, 2H), 7.59 (dd, J$_1$=J$_2$=7.2 Hz, 1H), 7.61-7.50 (m, 3H), 7.41 (s, 2H), 7.17 (d, J=2.0 Hz, 1H), 6.85 (dd, J$_1$=2.0 Hz and J$_2$=8.4 Hz, 1H), 5.16 (m, 1H), 4.98-4.95 (m, 1H), 4.31 (s, 2H), 4.25 (q, J=7.2 Hz, 2H), 3.96 (dd, J$_1$≈J$_2$=10.6 Hz, 1H), 3.88 (s, 6H), 3.80 (s, 3H), 3.62-1.96 (m, 16H) 1.30 (t, J=7.2 Hz, 3H).

MS m/z (+ESI): 814.6 [M+H]$^+$

Example 19

Preparation of methyl (1R,15S,17R,18R,19S,20S)-17-{[4-(butanoyloxy)-3,5-dimethoxyphenyl]carbonyloxy}-6,18-dimethoxy-3,13-diazapentacyclo[11.8.0.0$^{2,10}$.0$^{4,9}$.0$^{15,20}$]henicosa-2(10),4,6,8-tetraene-19-carboxylate

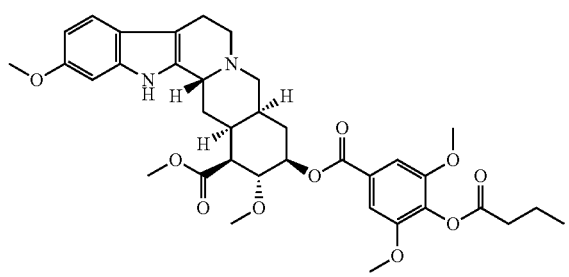 [SMILES: CCCC(=O)Oc1c(OC)cc(C(=O)O[C@@H]2C[C@@H]3CN4CCc5c([nH]c6cc(OC)ccc56)[C@H]4C[C@@H]3[C@H](C(=O)OC)[C@H]2OC)cc1OC]

0.13 mL of butyryl chloride (1.26 mmol, 5.0 eq.) are added dropwise to a solution of 150 mg of methyl (1R,15S, 17R,18R,19S,20S)-17-[(4-hydroxy-3,5-dimethoxyphenyl) carbonyloxy]-6,18-dimethoxy-3,13-diazapentacyclo [11.8.0.0$^{2,10}$.0$^{4,9}$.0$^{15,20}$]henicosa-2(10),4,6,8-tetraene-19-carboxylate (CAS 21432-74-6) (0.25 mmol, 1.0 eq.) in 2 mL of pyridine at 0° C. After agitation at 15° C. for 2 hours, the reaction mixture is concentrated under reduced pressure. The residue is purified by silica gel column chromatography eluting with DCM/methanol=1/20. The obtained crude product is further purified by preparative HPLC (eluent: water with 0.02% ammonia and acetonitrile; gradient) to give 26 mg of the desired product as solid.

$^1$H NMR (400 MHz, DMSO-d$_6$) δ ppm: 10.55 (s, 1H), 7.41 (s, 2H), 7.23 (d, J=8.0 Hz, 1H), 6.82 (s, 1H), 6.63 (d, J=8.0 Hz, 1H), 4.97 (m, 1H), 4.38 (m, 1H), 3.97 (dd, J$_1$=J$_2$=10.0 Hz, 1H), 3.87 (s, 6H), 3.81 (s, 3H), 3.76 (s, 3H), 3.43 (s, 3H), 3.06-1.66 (m, 17H), 1.03-1.01 (m, 3H).

LC-MS m/z (+ESI): 665.3 [M+H]$^+$

Example 20

Preparation of methyl (1R,15S,17R,18R,19S,20S)-17-({3,5-dimethoxy-4-[(2-phenylacetyl)oxy]phenyl}carbonyloxy)-6,18-dimethoxy-3,13-diazapentacyclo[11.8.0.0$^{2,10}$.0$^{4,9}$.0$^{15,20}$]henicosa-2(10),4,6,8-tetraene-19-carboxylate

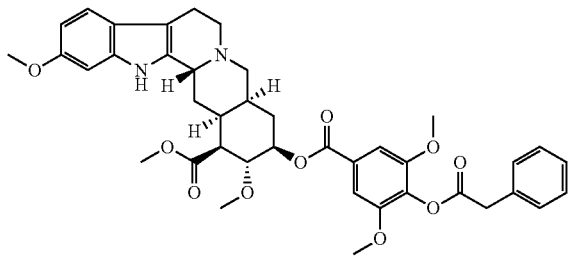 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)Cc3ccccc3)c(OC)c2)[C@@H]1OC]

A mixture containing 100 mg of methyl (1R,15S,17R,18R,19S,20S)-17-[(4-hydroxy-3,5-dimethoxyphenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate (CAS 21432-74-6) (0.17 mmol, 1.0 eq.), 28 mg of phenylacetic acid (0.2 mmol, 1.2 eq.), 60 mg of 1-ethyl-3-(3-dimethylaminopropyl)carbodiimide hydrochloride (0.34 mmol, 2.0 eq.), 10 mg of DMAP (0.08 mmol, 0.5 eq.) and 3 mL of DCM is stirred at 25° C. for 16 hours. Then the reaction mixture is concentrated under reduced pressure. The residue is purified by preparative HPLC (eluent: water with 0.02% ammonia and acetonitrile; gradient) to give 40 mg of the desired product as yellow solid.

$^1$H NMR (400 MHz, DMSO-d$_6$+D$_2$O) δ ppm: 10.60 (br, 1H), 7.38-7.31 (m, 7H), 7.25 (d, J=8.4 Hz, 1H), 6.85 (s, 1H), 6.63 (d, J=8.4 Hz, 1H), 4.93 (m, 1H), 4.48-4.43 (m, 1H), 3.98-1.82 (m, 30H)

LC-MS m/z (+ESI): 713.3 [M+H]$^+$

Example 21

(a) Preparation of 4-benzyloxycarbonyloxy-3,5-dimethoxy-benzoic acid

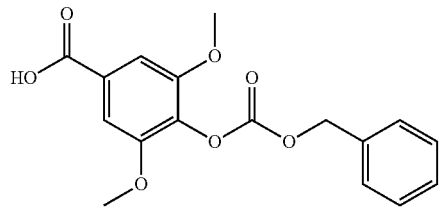 [SMILES: COc1cc(C(=O)O)cc(OC)c1OC(=O)OCc1ccccc1]

401 mg of benzyl chloroformate (2.35 mmol, 1.2 eq.) are added to a solution of 400 mg of 4-hydroxy-3,5-dimethoxybenzoic acid (1.96 mmol, 1 eq.) in 10 mL of pyridine. The reaction mixture is stirred at room temperature overnight. Then it is concentrated under reduced pressure, the residue is diluted with water, the mixture is acidified to pH 4 with 1 N hydrochloric acid and extracted with ethyl acetate. The organic phase is washed subsequently with 1 N hydrochloric acid and brine, dried over magnesium sulfate and concentrated under reduced pressure. The residue is purified by MCI gel chromatography (eluent: water/acetonitrile/TFA 4/1/0.1-1/2/0.1; v/v/v). After evaporation of the acetonitrile under reduced pressure, the aqueous phase is extracted with ethyl acetate, the organic phase is washed with brine, dried over magnesium sulfate, filtered and concentrated under reduced pressure to give 154 mg of the desired product as solid.

LC-MS m/z (+ESI): 333.3 [M+H]$^+$ (b) Preparation of methyl (1R,15S,17R,18R,19S,20S)-17-[(4-{[(benzyloxy)carbonyl]oxy}-3,5-dimethoxyphenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate

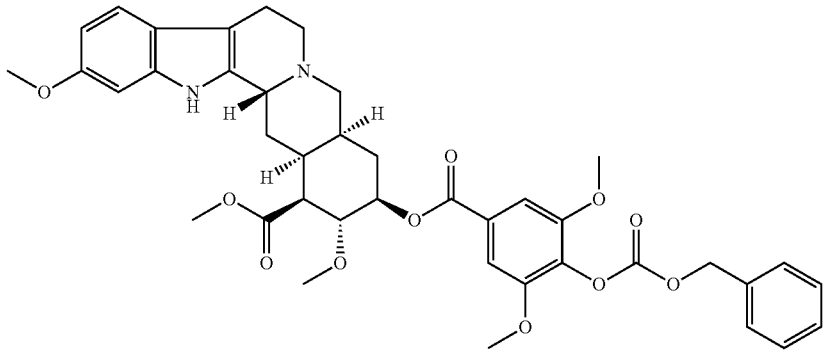 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3ccccc3)c(OC)c2)[C@@H]1OC]

150 mg of 4-benzyloxycarbonyloxy-3,5-dimethoxy-benzoic acid (0.45 mmol, 1 eq.), 113 mg of DMAP (0.9 mmol, 2 eq.) and 89 mg of benzenesulfonyl chloride (0.5 mmol, 1.1 eq.) are added to a solution of 187 mg of methyl (1R,15S,17R,18R,19S,20S)-17-hydroxy-6,18-dimethoxy-3,13-diazapentacyclo[11.8.0.0$^{2,10}$.0$^{4,9}$.0$^{15,20}$]henicosa-2(10),4,6,8-tetraene-19-carboxylate (CAS 2901-66-8) (0.45 mmol, 1 eq.) in DCM. The reaction mixture is stirred for 3 h at room temperature, diluted with DCM and washed subsequently with water, 5% aqueous citric acid solution, 5% aqueous sodium bicarbonate solution and brine. The organic phase is dried over magnesium sulfate, filtered and concentrated under reduced pressure. The crude product is treated with a mixture of DCM, ethyl acetate and diisopropylether, and the formed precipitate is further purified by preparative HPLC to give 108 mg of the desired product as light yellow solid.

$^1$H NMR (400 MHz, DMSO-d$_6$) δ ppm: 10.55 (s, 1H), 7.46-7.40 (m, 7H), 7.23 (d, J=8.4 Hz, 1H), 6.81 (d, J=2 Hz, 1H), 6.62 (dd, J$_1$=2.0 Hz and J$_2$=8.4 Hz, 1H), 5.31 (s, 2H), 4.99-4.92 (m, 1H), 4.36 (m, 1H), 3.97 (dd, J=J$_2$=10.0 Hz, 1H), 3.88 (s, 6H), 3.80 (s, 3H), 3.76 (s, 3H), 3.42 (s, 3H), 3.10-1.75 (m, 13H).

LC-MS m/z (+ESI): 729.6 [M+H]$^+$

Example 22

(a) Preparation of 3,5-dimethoxy-4-phenyloxycarbonyloxy benzoic acid

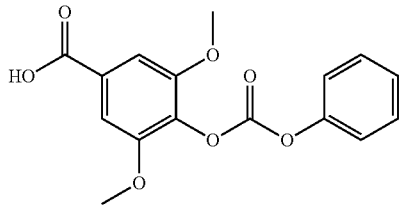

379 mg of phenyl chloroformate (2.35 mmol, 1.2 eq.) are added to a solution of 400 mg of 4-hydroxy-3,5-dimethoxy-benzoic acid (1.96 mmol, 1 eq.) in 10 mL of pyridine. The reaction mixture is stirred at room temperature for 3 h. Then it is concentrated under reduced pressure, the residue is diluted with water, the mixture is acidified to pH 4 with 1 N hydrochloric acid and extracted with ethyl acetate. The organic phase is washed subsequently with 1 N hydrochloric acid and brine, dried over magnesium sulfate and concentrated under reduced pressure. The residue is purified by MCI gel chromatography (eluent: water/acetonitrile/TFA 4/1/0.1-1/2/0.1; v/v/v). After evaporation of the acetonitrile under reduced pressure, the aqueous phase is extracted with ethyl acetate, the organic phase is washed with brine, dried over magnesium sulfate, filtered and concentrated under reduced pressure to give 133 mg of the desired product as solid.

LC-MS m/z (+ESI): 319.3 [M+H]$^+$

(b) Preparation of methyl (1R,15S,17R,18R,19S,20S)-17-({3,5-dimethoxy-4-[(phenoxycarbonyl)oxy]phenyl}carbonyloxy)-6,18-dimethoxy-3,13-diaza-pentacyclo[11.8.0.0$^{2,10}$.0$^{4,9}$.0$^{15,20}$]henicosa-2(10),4,6,8-tetraene-19-carboxylate

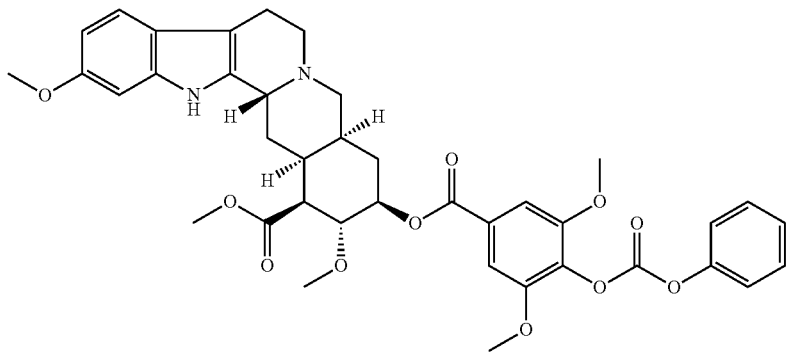 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)Oc3ccccc3)c(OC)c2)[C@@H]1OC]

100 mg of 3,5-dimethoxy-4-phenyloxycarbonyloxy benzoic acid (0.31 mmol, 1 eq.), 78 mg of DMAP (0.63 mmol, 2 eq.) and 62 mg of benzenesulfonyl chloride (0.35 mmol, 1.1 eq.) are added to a solution of 130 mg of methyl (1R,15S,17R,18R,19S,20S)-17-hydroxy-6,18-dimethoxy-3,13-diazapentacyclo[11.8.0.0$^{2,10}$.0$^{4,9}$.0$^{15,20}$]henicosa-2(10),4,6,8-tetraene-19-carboxylate (CAS 2901-66-8) (0.31 mmol, 1 eq.) in DCM. The reaction mixture is stirred for 3 h at room temperature, diluted with DCM and washed subsequently with water, 5% aqueous citric acid solution, 5% aqueous sodium bicarbonate solution and brine. The organic phase is dried over magnesium sulfate, filtered and concentrated under reduced pressure. The crude product is treated with a mixture of DCM and diisopropylether, and the formed precipitate is filtered and dried under vacuum to give 26 mg of the desired product as light brown solid.

$^1$H NMR (400 MHz, DMSO-d$_6$) δ ppm: 10.55 (s, 1H), 7.53-7.31 (m, 7H), 7.23 (d, J=8.4 Hz, 1H), 6.81 (d, J=2 Hz, 1H), 6.62 (dd, J$_1$=2.0 Hz and J$_2$=8.4 Hz, 1H), 5.01-4.92 (m, 1H), 4.36 (m, 1H), 4.00-3.95 (m, 1H), 3.97 (s, 6H), 3.81 (s, 3H), 3.76 (s, 3H), 3.43 (s, 3H), 3.10-1.75 (m, 13H).

LC-MS m/z (+ESI): 715.4 [M+H]$^+$

Examples 23 to 29
The following compounds are prepared according to the synthetic method described for Example 20:
Example 23
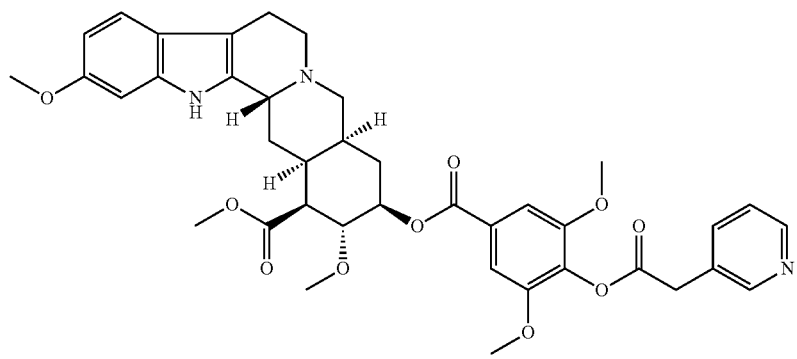 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)Cc3cccnc3)c(OC)c2)[C@@H]1OC]
Example 24
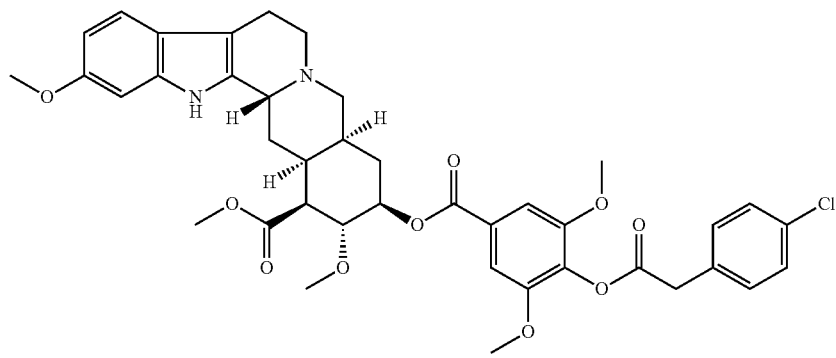 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)Cc3ccc(Cl)cc3)c(OC)c2)[C@@H]1OC]
Example 25
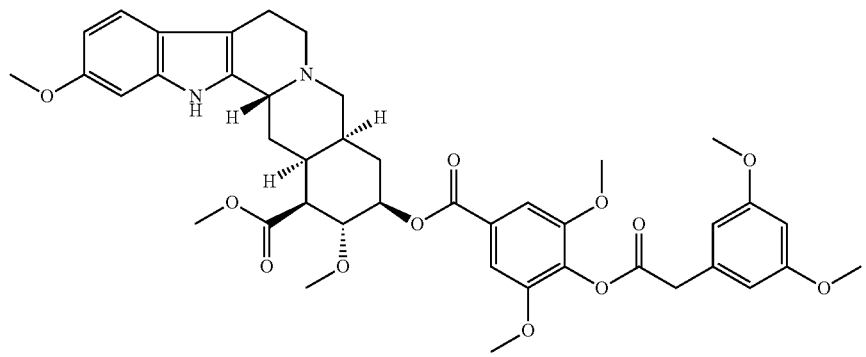

Example 26
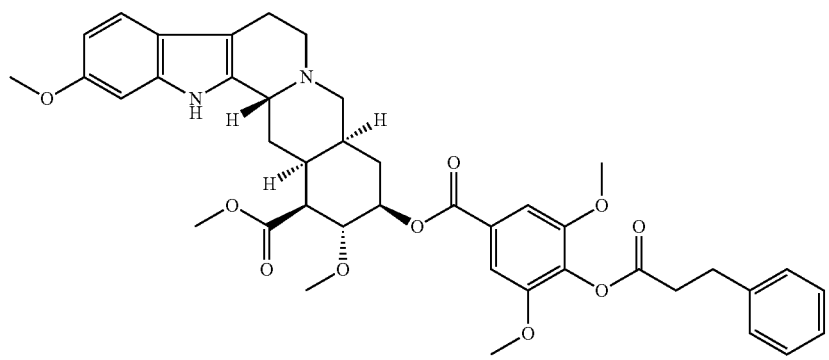 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)CCc3ccccc3)c(OC)c2)[C@@H]1OC]
Example 27
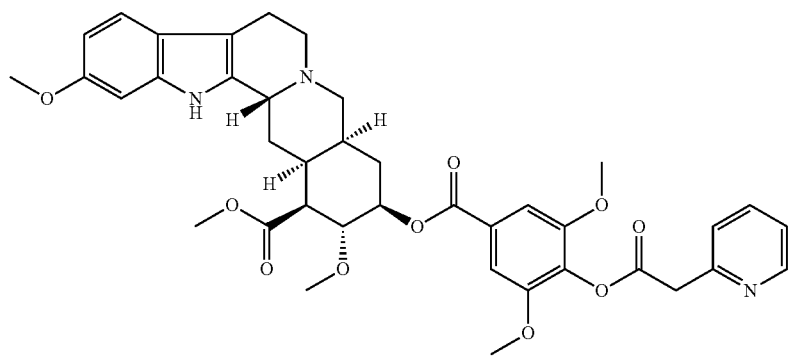 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)Cc3ccccn3)c(OC)c2)[C@@H]1OC]
Example 28
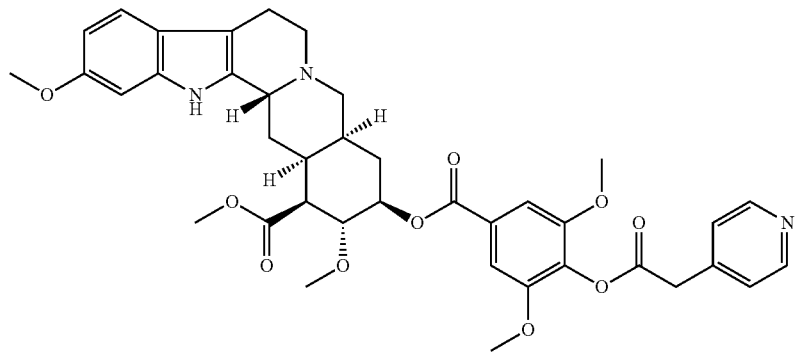 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)Cc3ccncc3)c(OC)c2)[C@@H]1OC]

Example 29

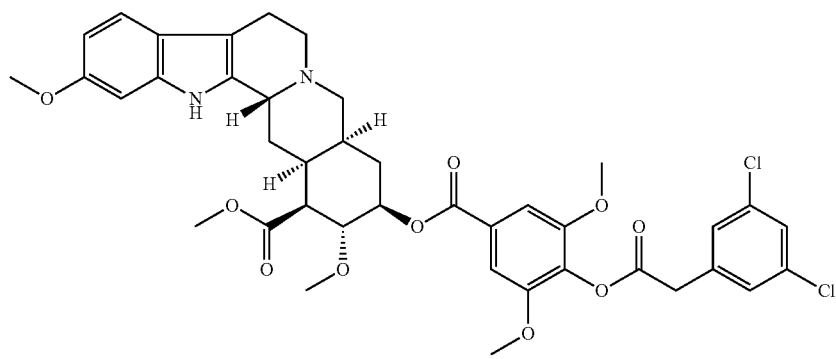 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)Cc3cc(Cl)cc(Cl)c3)c(OC)c2)[C@@H]1OC]

Examples 33 to 44

Following compounds are prepared via the corresponding 4-nitrophenylcarbonates from (1R,15S,17R,18R,19S,20S)-17-[(4-hydroxy-3,5-dimethoxyphenyl)carbonyloxy]-6,18-dimethoxy-3,13-diazapentacyclo[11.8.0.0$^{2,10}$.0$^{4,9}$.0$^{15,20}$]henicosa-2(10),4,6,8-tetraene-19-carboxylate (CAS 21432-74-6) according to the synthetic method described for Example 6:

Example 42 is prepared by using 3-[[(1,1-dimethylethyl)dimethylsilyl]oxy]-benzenemethanol (CAS 96013-77-3) and final cleavage of the silylether using potassium carbonate in DMF.

Example 44 is prepared by using 3-nitro-benzenemethanol (CAS 619-25-0) and final Fe/FeSO$_4$ mediated reduction of the nitro-group

Example 30

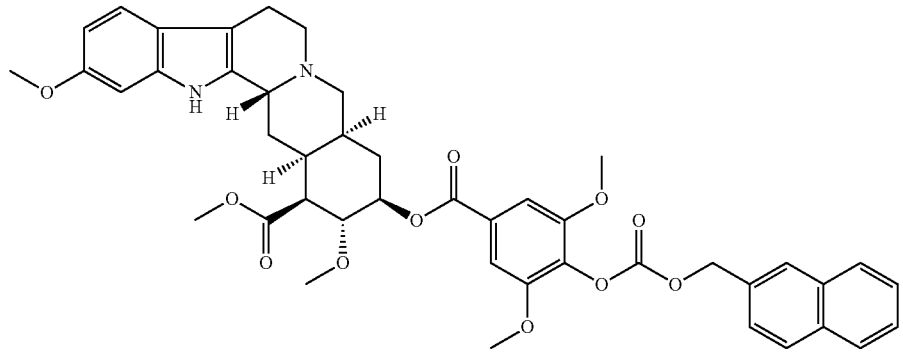 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3ccc4ccccc4c3)c(OC)c2)[C@@H]1OC]

Example 31

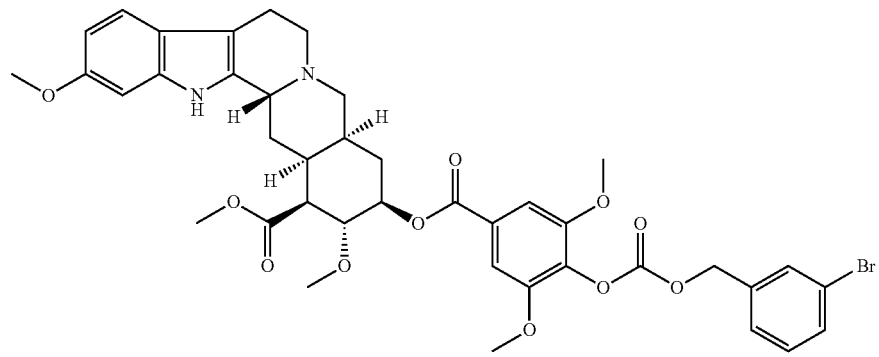 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3cccc(Br)c3)c(OC)c2)[C@@H]1OC]

Example 32
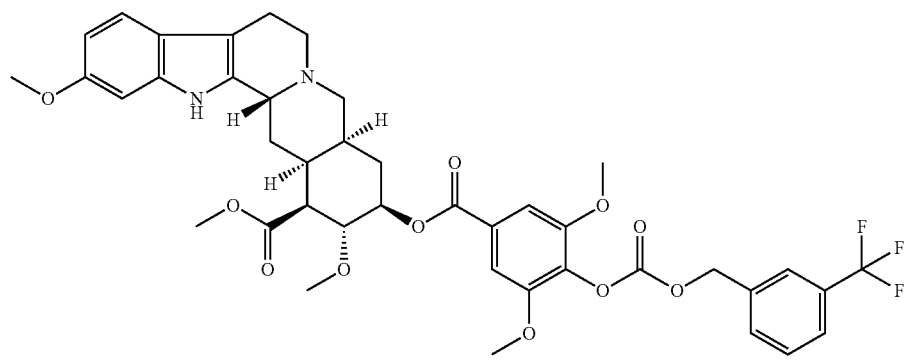 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3cccc(C(F)(F)F)c3)c(OC)c2)[C@@H]1OC]
Example 33
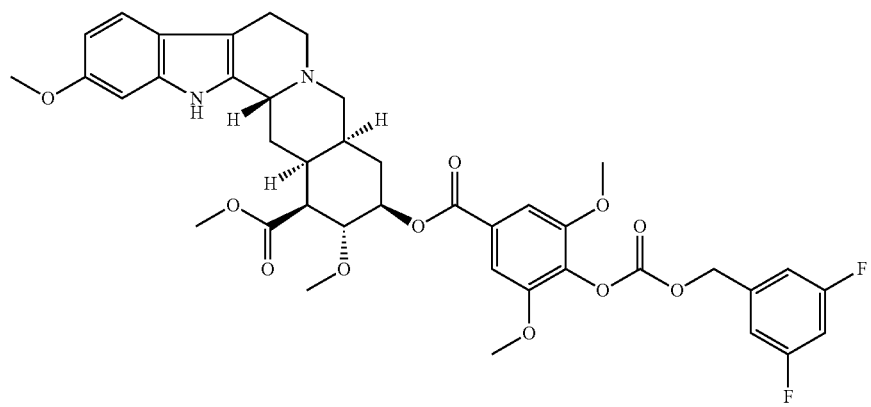 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3cc(F)cc(F)c3)c(OC)c2)[C@@H]1OC]
Example 34
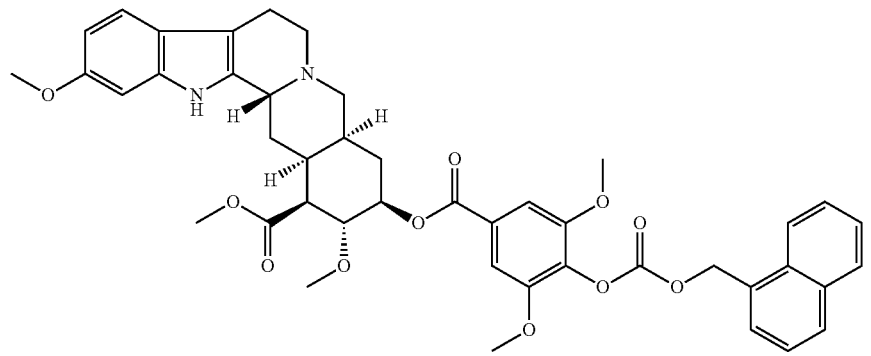 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3cccc4ccccc34)c(OC)c2)[C@@H]1OC]

Example 35
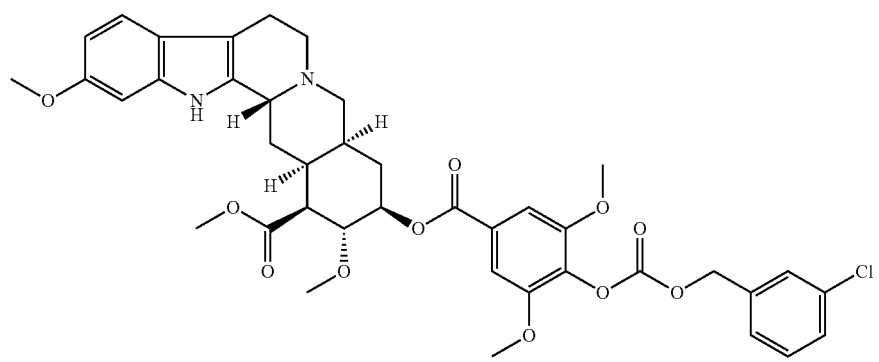 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3cccc(Cl)c3)c(OC)c2)[C@@H]1OC]
Example 36
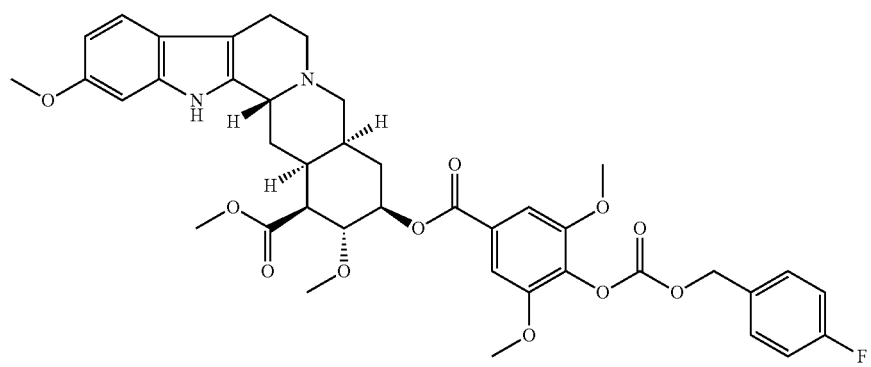 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3ccc(F)cc3)c(OC)c2)[C@@H]1OC]
Example 37
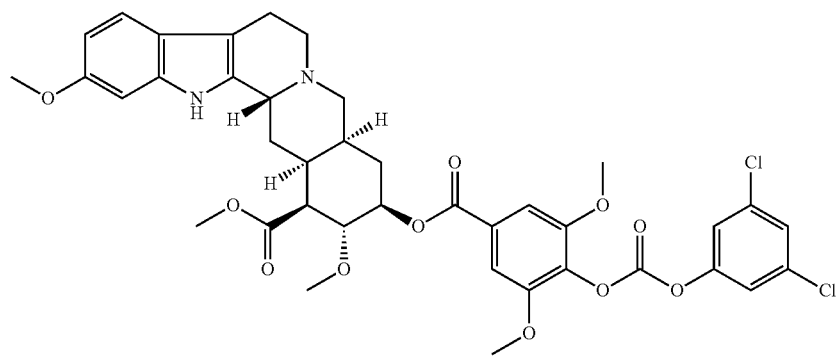 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)Oc3cc(Cl)cc(Cl)c3)c(OC)c2)[C@@H]1OC]

Example 38
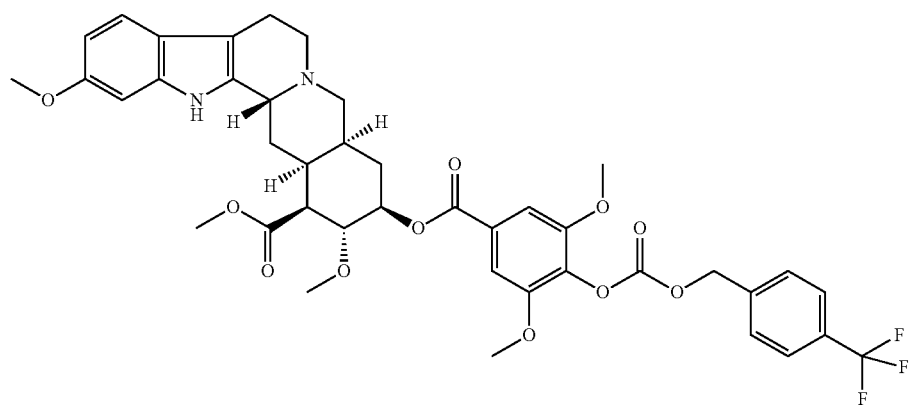 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3ccc(C(F)(F)F)cc3)c(OC)c2)[C@@H]1OC]
Example 39
Example 40

Example 41
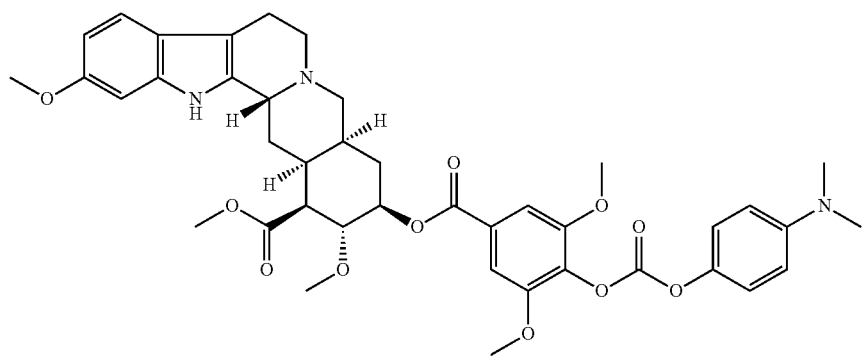
Example 42
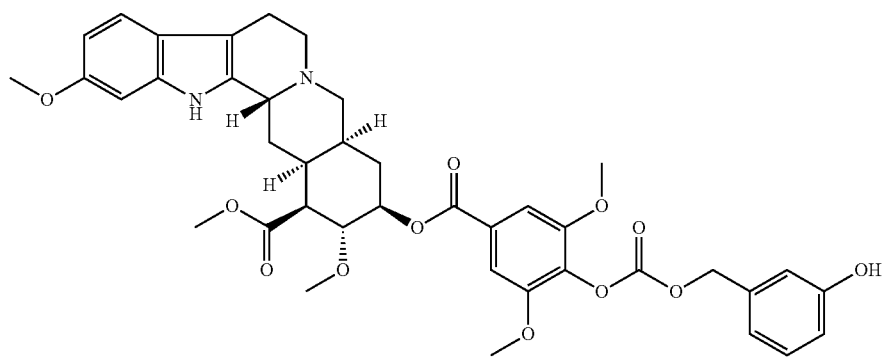 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3cccc(O)c3)c(OC)c2)[C@@H]1OC]
Example 43
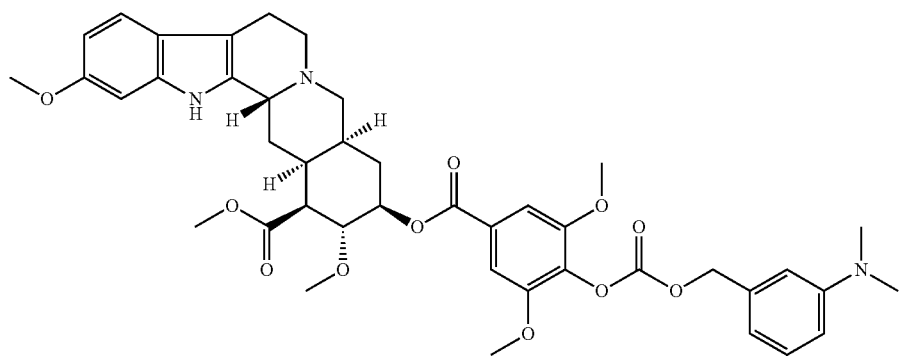

Example 44

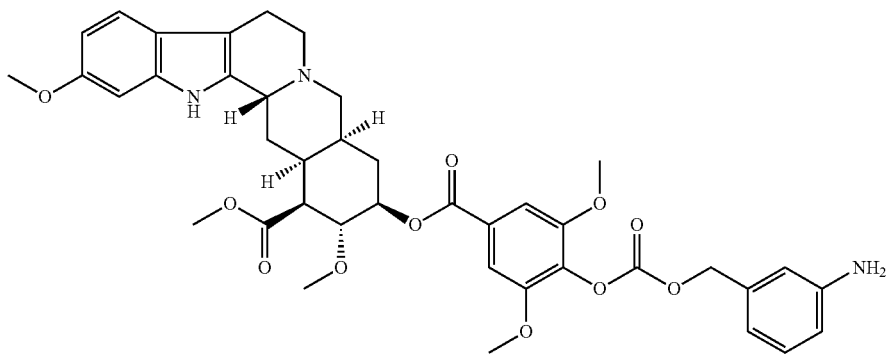 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3cccc(N)c3)c(OC)c2)[C@@H]1OC]

Analytical Data:

| Example | $^1$H NMR (400 MHz, DMSO-$d_6$) δ ppm | LC-MS m/z (+ESI) [M + H]$^+$ |
|---|---|---|
| 23 | 8.69 (d, J = 1.6 Hz, 1H), 8.63 (dd, $J_1$ = 1.2 Hz, $J_2$ = 5.2 Hz, 1H), 8.08 (m, 1H), 7.68 (m, 1H), 7.38-7.35 (m, 3H), 6.88 (d, J = 2.4 Hz, 1H), 6.70 (dd, J = 2.4 Hz, $J_2$ = 8.8 Hz, 1H), 5.08 (s, 1H), 4.95-4.85 (m, 1H), 4.17 (s, 2H), 3.90 (dd, $J_1 \approx J_2$ = 10.0 Hz, 1H), 3.81 (s, 6H), 3.79 (s, 3H), 3.75 (s, 3H), 3.60-1.91 (m, 16H) | 714.2 |
| 24 | 7.45-7.36 (m, 6H), 7.23 (d, J = 8.4 Hz, 1H), 6.80 (d, J = 2.0 Hz, 1H), 6.61 (dd, $J_1$ = 2.0 Hz, $J_2$ = 8.4 Hz, 1H), 4.93-4.92 (m, 1H), 4.91 (m, 1H), 3.99 (s, 2H), 3.92 (dd, $J_1 \approx J_2$ = 10.8 Hz, 1H), 3.81 (s, 6H), 3.77 (s, 3H), 3.73 (s, 3H), 3.39 (s, 3H), 3.07-1.75 (m, 13H) | 747.2 |
| 25 | 10.53 (s, 1H), 7.39 (s, 2), 7.22 (d, J = 8.8 Hz, 1H), 6.80 (d, J = 2.4 Hz, 1H), 6.61 (dd, $J_1$ = 2.4 Hz, $J_2$ = 8.8 Hz, 1H), 6.56 (d, J = 2.0 Hz, 2H), 6.44 (dd, $J_1$ = $J_2$ = 2.0 Hz, 1H), 4.96-4.94 (m, 1H), 4.35 (m, 1H), 3.98-3.91 (m, 3H), 3.84 (s, 6H), 3.79 (s, 3H), 3.77-3.73 (m, 9H), 3.41 (s, 3H), 3.04-1.78 (m, 13H) | 773.3 |
| 26 | 10.99 (s, 1H), 7.38-7.21 (m, 8H), 6.89 (d, J = 2.4 Hz, 1H), 6.70 (dd, $J_1$ = 2.4 Hz, $J_2$ = 8.8 Hz, 1H), 5.05 (m, 1H), 4.92 (m, 1H), 3.90 (dd, $J_1 \approx J_2$ = 10.0 Hz, 1H), 3.79-3.74 (m, 9H), 3.57-1.94 (m, 20H) | 727.3 |
| 27 | 8.58 (dd, J1 = 0.8 Hz, $J_2$ = 4.8 Hz, 1H), 7.90 (dd, $J_1 \approx J_2$ = 8.0 Hz, 1H), 7.53 (d, J = 8.0 Hz, 1H), 7.44-7.40 (m, 1H), 7.38-7.35 (m, 3H), 6.88 (d, J = 2.4 Hz, 1H), 6.70 (dd, $J_1$ = 2.4 Hz, $J_2$ = 8.4 Hz, 1H), 5.07 (s, 1H), 4.95-4.85 (m, 1H), 3.92 (dd, $J_1 \approx J_2$ = 9.6 Hz, 1H), 3.81 (s, 6H), 3.79 (s, 3H), 3.75 (s, 3H), 3.57-1.93 (m, 16H) | 714.3 |
| 28 | 8.72 (d, J = 6.4 Hz, 2H), 7.72 (d, J = 6.4 Hz, 2H), 7.37-7.35 (m, 3H), 6.88 (d, J = 2.0 Hz, 1H), 6.71 (dd, $J_1$ = 2.0 Hz, $J_2$ = 8.8 Hz, 1H), 5.07 (s, 1H), 4.93 (m, 1H), 3.92 (dd, $J_1 \approx J_2$ = 10.0 Hz, 1H), 3.82 (s, 6H), 3.75 (s, 3H), 3.65-1.91 (m, 15H) | 714.3 |
| 29 | 11.00 (s, 1H), 7.55 (dd, $J_1$ = $J_2$ = 1.6 Hz, 1H), 7.45 (d, J = 1.6 Hz, 2H), 7.38-7.35 (m, 3H), 6.88 (d, J = 2.0 Hz, 1H), 6.70 (dd, $J_1$ = 2.0 Hz, J2 = 8.4 Hz, 1H), 5.07 (s, 1H), 4.95-4.93 (m, 1H), 4.06 (s, 2H), 3.92 (dd, $J_1 \approx J_2$ = 9.6 Hz, 1H), 3.83 (s, 6H), 3.79 (s, 3H), 3.75 (s, 3H), 3.57-1.92 (m, 16H) | 781.1 |
| 30 | 10.53 (s, 1H), 7.95-8.01 (m, 4H), 7.54-7.58 (m, 3H), 7.42 (s, 2H), 7.22 (d, J = 8.4 Hz, 1H), 6.80 (d, J = 2.0 Hz, 1H), 6.61 (dd, J = 2.0, 8.4 Hz, 1H), 5.47 (s, 2H), 4.93 (m, 1H), 4.32 (m, 1H), 3.96 (m, 1H), 3.87 (s, 6H), 3.75 + 3.80 (2s, 6H), 3.32 (s, 3H), 1.80-3.05 (m, 13H) | 779.1 |
| 31 | 10.53 (s, 1H), 7.61 (m, 2H), 7.42 (m, 4H), 7.22 (d, J = 8.4 Hz, 1H), 6.80 (d, J = 2.4 Hz, 1H), 6.61 (dd, J = 2.0, 8.4 Hz, 1H), 5.30 (s, 2H), 4.95 (m, 1H), 4.35 (m, 1H), 3.96 (m, 1H), 3.88 (s, 6H), 3.75 + 3.79 (2s, 6H), 3.41 (s, 3H), 1.70-3.15 (m, 13H) | 807.0 + 809.0 |
| 32 | 10.53 (s, 1H), 7.68-7.80 (m, 4H), 7.43 (s, 2H), 7.22 (d, J = 8.4 Hz, 1H), 6.80 (s, 1H), 6.61 (dd, J = 2.4 + 8.4 Hz, 1H), 5.30 (s, 2H), 4.95 (m, 1H), 4.35 (m, 1H), 3.96 (m, 1H), 3.88 (s, 6H), 3.75 + 3.79 (2s, 6H), 3.41 (s, 3H), 1.70-3.10 (m, 13H) | 797.2 |

-continued

| Example | $^1$H NMR (400 MHz, DMSO-$d_6$) δ ppm | LC-MS m/z (+ESI) [M + H]$^+$ |
|---|---|---|
| 33 | 10.54 (br, 1H), 7.42 (s, 2H), 7.12-7.32 (m, 4H), 6.80 (d, J = 2.4 Hz, 1H), 6.61 (dd, J = 2.2, 8.6 Hz, 1H), 5.33 (s, 2H), 4.96 (m, 1H), 4.35 (s, 1H), 3.96 (m, 1H), 3.89 (s, 6H), 3.79 + 3.75 (2s, 6H), 3.41 (s, 3H), 1.74-3.05 (m, 13H) | 765.2 |
| 34 | 10.53 (br, 1H), 8.04 (m, 3H), 7.53-7.70 (m, 4H), 7.39 (s, 2H), 7.22 (d, J = 8.4 Hz, 1H), 6.80 (s, 1H), 6.61 (d, J = 8.4 Hz, 1H), 5.78 (s, 2H), 4.95 (m, 1H), 4.35 (s, 1H), 3.95 (m, 1H), 3.84 (s, 6H), 3.79 + 3.75 (2s, 6H), 3.40 (s, 3H), 1.73-3.10 (m, 13H) | 779.2 |
| 35 | 10.54 (br, 1H), 7.39-7.49 (m, 4H), 7.39 (s, 2H), 7.22 (d, J = 8.4 Hz, 1H), 6.80 (d, J = 2.4 Hz, 1H), 6.61 (dd, J = 2.2 + 8.2 Hz, 1H), 5.31 (s, 2H), 4.95 (m, 1H), 4.35 (s, 1H), 3.96 (m, 1H, 3.88 (s, 6H), 3.79 + 3.75 (2s, 6H), 3.40 (s, 3H), 1.73-3.07 (m, 13H) | 763.1 |
| 36 | 10.53 (br, 1H), 7.50 (m, 2H), 7.41 (s, 2H), 7.19-7.31 (m, 4H), 6.80 (d, J = 2.0 Hz, 1H), 6.61 (dd, J = 2.2 + 8.8 Hz, 1H), 5.28 (s, 2H), 4.91 (m, 1H), 4.35 (s, 1H), 3.96 (m, 1H), 3.87 (s, 6H), 3.75 + 3.79 (2s, 6H), 3.40 (s, 3H), 1.74-3.06 (m, 13H) | 747.1 |
| 37 | 10.55 (br, 1H), 7.68 (s, 1H), 7.57 (d, J = 1.2 Hz, 2H), 7.46 (s, 2H), 7.23 (d, J = 8.4 Hz, 1H), 6.80 (s, 1H), 6.62 (d, J = 8.4 Hz, 1H), 4.95 (m, 1H), 4.35 (s, 1H), 3.97 (m, 1H), 3.96 (s, 6H), 3.75 + 3.80 (2s, 6H), 3.41 (s, 3H), 1.77-3.10 (m, 13H) | 783.2 |
| 38 | 10.54 (br, 1H), 7.83 (d, J = 8.4 Hz, 2H), 7.65 (d, J = 8.0 Hz, 2H), 7.42 (s, 2H), 7.22 (d, J = 8.4 Hz, 1H), 6.80 (d, J = 2.4 Hz, 1H), 6.60 (dd, J = 2.4, 8.4 Hz, 1H), 5.41 (s, 2H), 4.96 (m, 1H), 4.35 (m, 1H), 3.95 (m, 1H), 3.88 (s, 6H), 3.75 + 3.79 (2s, 6H), 3.40 (s, 3H), 1.70-3.10 (m, 13H) | 797.1 |
| 39 | 10.54 (br, 1H), 7.45 (s, 2H), 7.22 (d, J = 8.4 Hz, 1H), 6.80 (d, J = 2.0 Hz, 1H), 6.60 (dd, J = 2.0 + 8.4 Hz, 1H), 6.48 (m, 3H), 4.97 (m, 1H), 4.35 (m, 1H), 3.95 (m, 7H), 3.75-3.85 (m, 12H), 3.41 (s, 3H), 1.75-3.10 (m, 13H) | 775.1 |
| 40 | 10.54 (br, 1H), 7.45 (s, 2H), 7.18-7.30 (m, 2H), 6.80 (s, 1H), 6.50-6.70 (m, 4H), 4.96 (m, 1H), 4.35 (m, 1H), 3.95 (m, 7H), 3.75 + 3.79 (2s, 6H), 2.93 (s, 6H), 1.75-3.10 (m, 13H) | 758.3 |
| 41 | 10.55 (br, 1H), 7.44 (s, 2H), 7.22 (d, 1H, J = 8.4 Hz), 7.10 (d, 2H, J = 2.0 + 7.2 Hz), 6.80 (d, 1H, J = 2.4 Hz), 6.75 (dd, 2H, J = 2.0 + 7.2 Hz), 6.61 (d, 1H, J = 2.4 + 8.4 Hz), 4.95 (m, 1H), 4.35 (m, 1H), 3.95 (m, 7H, CH-17), 3.75 + 3.80 (2s, 6H), 3.41 (s, 3H), 2.90 (s, 6H), 1.70-3.10 (m, 13H) | 758.3 |
| 42 | 11.04 (br, 1H), 9.57 (br, 1H), 7.41 (s, 2H), 7.38 (m, 1H), 7.22 (dd, J$_1$ = J$_2$ = 8.0 Hz, 1H), 6.70-6.90 (m, 5H), 5.21 (s, 2H), 5.11 (m, 1H), 4.97 (m, 1H), 3.95 (m, 1H), 3.88 (s, 6H), 3.78 + 3.82 (2s, 6H), 3.40 (s, 3H) 1.90-3.30 (m, 13H) | 745.5 |
| 43 | 10.53 (br, 1H), 7.41 (s, 2H), 7.22 (m, 2H), 6.60-6.80 (m, 5H), 5.22 (s, 2H), 4.95 (m, 1H), 4.34 (m, 1H), 3.95 (m, 1H), 3.87 (s, 6H), 3.75 + 3.79 (2s, 6H), 3.41 (s, 3H), 1.70-3.10 (m, 19H) | 772.6 |
| 44 | 10.53 (br, 1H), 7.41 (s, 2H), 7.22 (d, J = 8.4 Hz, 1H), 7.05 (dd, J$_1$ = J$_2$ = 8.0 Hz, 1H), 6.80 (d, J = 1.6 Hz, 1H), 6.50-6.65 (m, 4H), 5.19 (br, 2H), 5.12 (s, 2H), 4.95 (m, 1H), 4.34 (m, 1H), 3.95 (m, 1H), 3.88 (s, 6H), 3.75 + 3.80 (2s, 6H), 3.41 (s, 3H), 1.70-3.10 (m, 13H) | 744.6 |

Biological Activity Assays

The in vitro anti-proliferative activity of compounds of formula (I), metformin and combinations thereof is tested in an AlamarBlue conversion cell proliferation assay (Promega) on HL60 tumor cells and the mouse mast cell line 6.5 (Colombi et al., Oncogene 2011, 30:1551-65). Cells are seeded into 96-well microtiter plates (seeding cell density is 7,000 cells per well in 150 uL Iscove's medium) and test compounds are added (compounds of formula (I) are added from a 10 mM stock solution in DMSO, metformin from a freshly prepared 1 M solution in culture medium). Plates are incubated for 3 days at 37°, 5% $CO_2$ and proliferation is determined by AlamarBlue staining (0.1 vol % added to cultures and incubated for further 4-5 hours). The conversion of AlamarBlue is proportional to live cell number and is read with a fluorescence plate reader (Ex/Em 535/595 nm). Growth is normalized to the untreated controls.

The same assay conditions can be used for testing the anti-proliferative activity of compounds of formula (I) in combination with other inhibitors of mitochondrial function like rotenone, piericidin A, epiberberine, 2-thenoyltrifluoroacetone (TTFA), sodium malonate, antimycin A, KCN, sodium azide, oligomycin, carbonyl cyanide-p-trifluoromethoxyphenylhydrazone (FCCP) or stavudine, each used at its appropriate concentration.

Results:

Metformin at 4 mM and all exemplified compounds of formula (I) at concentrations up to 10 μM do not show significant anti-proliferative activity on their own. When the exemplified compounds of formula (I) at concentrations of 10 μM and lower are combined with 4 mM of metformin, a strong anti-proliferative activity is observed. The Compound of Example 6-10, 12-18, 20-21, 31-36, 38 of the present application e.g. exhibit an anti-proliferative activity in combination with 4 mM metformin at concentrations of 5 μM and lower. The following Table lists the concentration of said compounds in micromols that inhibit the proliferation of cells in the described assays by approximately 50% when combined with 4 mM metformin:

| Example | 6.5 cell line [μM] | HL60 cell line [μM] |
|---|---|---|
| 6 | 2.5 | 2.5 |
| 7 | 2.5 | 2 |
| 8 | 5 | 4 |
| 9 | 4 | 4 |
| 10 | 1 | 1 |
| 12 | 1.5 | 1.5 |
| 13 | 1 | 2 |
| 14 | 1.5 | 2 |
| 15 | 1.5 | 2 |
| 16 | 1 | 2 |
| 17 | 1 | 1.5 |
| 18 | 1 | 1.5 |
| 20 | 5 | 5 |
| 21 | 2 | 3.5 |
| 31 | 2 | 2 |
| 32 | 2 | 2 |
| 33 | 2 | 2 |
| 34 | 7.5 | 5 |
| 35 | 2 | 2 |
| 36 | 2.5 | 3 |
| 38 | 4 | 4 |

The invention claimed is:

1. A compound of formula (I):

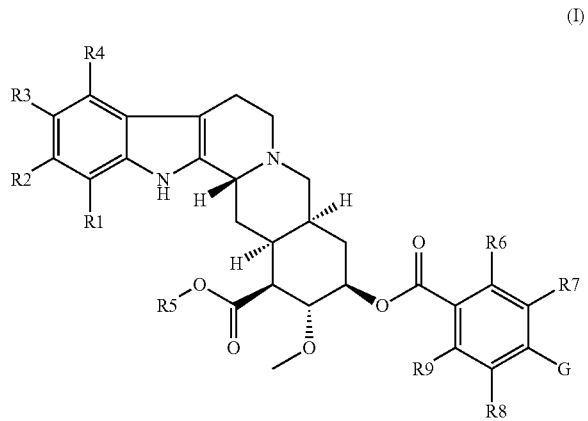

(I)

wherein:
R1, R3 and R4 represent hydrogen;
R2 represents a group —OR2a;
R2a represents hydrogen, methyl or a group selected from $C_1$-$C_4$alkylcarbonyl, $C_1$-$C_4$alkoxycarbonyl and phenylcarbonyl, wherein $C_1$-$C_4$ alkylcarbonyl is unsubstituted or substituted with a group —NR11R10, wherein
R11 represents hydrogen or $C_1$-$C_4$alkyl and
R10 represents hydrogen, $C_1$-$C_4$alkyl, $C_1$-$C_4$alkylcarbonyl or phenylcarbonyl;
R5 represents methyl
R6 and R9 both represent hydrogen and
R7 and R8 independently of one another represent hydrogen or methoxy;
G represents a group selected from:
—OCO$_2$(CH$_2$)$_n$-A1, —OC(=O)CH$_2$-A2, —CH$_2$OC(=O)-A2, —CH$_2$OCO$_2$-A2, —CH$_2$NHCO$_2$-A2 and —CH$_2$CO$_2$-A2, wherein
A1 represents an optionally substituted group selected from $C_1$-$C_4$alkyl, $C_6$-$C_{10}$aryl, $C_5$-$C_{10}$heteroaryl, $C_3$-$C_7$cycloalkyl and $C_5$-$C_7$heterocyclyl,
A2 represents an optionally substituted group selected from $C_1$-$C_4$alkyl, $C_3$-$C_7$cycloalkyl, $C_5$-$C_7$heterocyclyl, —(CH$_2$)$_n$—$C_6$-$C_{10}$aryl and —(CH$_2$)$_n$—$C_5$-$C_{10}$heteroaryl and
n represents 0 or 1; and optionally present substituents referred to are selected from the group consisting of halogen, hydroxyl, $C_1$-$C_3$ alkyl, trifluoromethyl, $C_1$-$C_3$ alkoxy, amino, $C_1$-$C_3$ alkylamino, $C_1$-$C_3$ dialkylamino, cyano and carboxy;
with the proviso that R2 must not be methoxy when A1 is $C_1$-$C_4$alkyl.

2. The compound as claimed in claim 1, wherein
R2a represents methyl.

3. The compound as claimed in claim 1, wherein
A1 represents an optionally substituted group selected from $C_6$-$C_{10}$aryl and $C_5$-$C_{10}$ heteroaryl; and
A2 represents an optionally substituted group selected from $C_1$-$C_4$alkyl, —(CH$_2$)$_n$—$C_6$-$C_{10}$aryl and —(CH$_2$)$_n$—$C_5$-$C_{10}$heteroaryl.

4. The compound as claimed in claim 3, wherein
A1 represents pyridyl, phenyl or naphthyl, optionally substituted with amino, halogen, trifluoromethyl or methoxy; and
A2 represents $C_1$-$C_4$ alkyl.

5. The compound as claimed in claim 1, wherein
G is —OCO$_2$(CH$_2$)$_n$-A1;
A1 represents an optionally substituted group selected from $C_6$-$C_{10}$aryl and $C_5$-$C_{10}$heteroaryl; and
n is 1.

6. The compound as claimed in claim 1, wherein R11 represents hydrogen.

7. The compound as claimed in claim 1, wherein
G is —OCO$_2$(CH$_2$)$_n$-A1;
n represents 0 and
A1 represents $C_1$-$C_4$alkyl.

8. A method for the treatment of cancer or an autoimmune disease or for providing an immunosuppressive treatment to a warm-blooded animal or a human requiring such treatment, wherein a compound of formula (I):

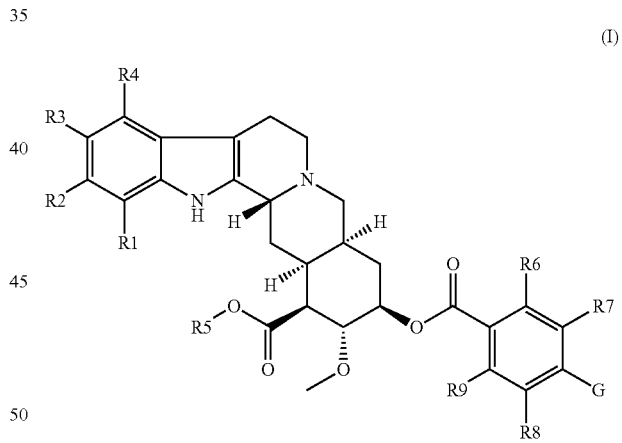

(I)

with the exception of syrosingopine,
wherein:
R1, R3 and R4 represent hydrogen;
R2 represents a group —OR2a;
R2a represents hydrogen, $C_1$-$C_3$ alkyl, or a group selected from $C_1$-$C_4$ alkylcarbonyl, $C_1$-$C_4$ alkoxycarbonyl and phenylcarbonyl, wherein $C_1$-$C_4$ alkylcarbonyl is unsubstituted or substituted with a group —NR11R10, wherein
R11 represents hydrogen or $C_1$-$C_4$alkyl and
R10 represents hydrogen, $C_1$-$C_4$alkyl, $C_1$-$C_4$alkylcarbonyl or phenylcarbonyl;
R5 represents methyl;
R6 and R9 both represent hydrogen and
R7 and R8 independently of one another represent hydrogen or methoxy;

G represents a group selected from:
—OCO$_2$(CH$_2$)$_n$-A1, —OC(=O)CH$_2$-A2, —CH$_2$OC(=O)-A2, —CH$_2$OCO$_2$-A2, —CH$_2$NHCO$_2$-A2 and —CH$_2$CO$_2$-A2, wherein A1 represents an optionally substituted group selected from C$_1$-C$_4$alkyl, C$_3$-C$_7$aryl, C$_5$-C$_7$heteroaryl, C$_3$-C$_7$cycloalkyl and C$_5$-C$_7$heterocyclyl, A2 represents an optionally substituted group selected from C$_1$-C$_4$alkyl, C$_3$-C$_7$cycloalkyl, C$_5$-C$_7$heterocyclyl, C$_6$-C$_{10}$aryl and —(CH$_2$)$_n$—C$_5$-C$_{10}$heteroaryl and n represents 0 or 1; and optionally present substituents referred to are selected from the group consisting of halogen, hydroxyl, C$_1$-C$_3$ alkyl, trifluoromethyl, C$_1$-C$_3$ alkoxy, amino, C$_1$-C$_3$ alkylamino, C$_1$-C$_3$ dialkylamino, cyano and carboxy;

is administered to said warm-blooded animal or human in combination with a mitochondrial inhibitor, selected from metformin, buformin and phenformin, in quantities of the combination partners which are effective against said cancer or autoimmune disease or for the immunosuppressive treatment.

9. The method of claim 8, wherein the mitochondrial inhibitor comprises metformin.

10. The method of claim 8, wherein the relative dosage (weight per weight) of the compound of formula (I) and the mitochondrial inhibitor is between 1 to 10 and 1 to 1,000.

11. The method of claim 10, wherein the relative dosage (weight per weight) of the compound of formula (I) and the metformin is between 1 to 10 and 1 to 200.

12. The method of claim 8, wherein the autoimmune disease is selected from autoimmune diseases of the skin, nervous system, connective tissue, muscle, nervous system, blood forming system, bone and inner organs.

13. The method of claim 8, wherein the compound of formula (I) is administered separately before or after administration of the mitochondrial inhibitor.

14. The method of claim 8, wherein the compound of formula (I) and the mitochondrial inhibitor are administered simultaneously.

15. A pharmaceutical product comprising a compound of formula (I):

(I)

with the exception of syrosingopine,
wherein:
R1, R3 and R4 represent hydrogen;
R2 represents a group —OR2a;
R2a represents hydrogen, methyl or a group selected from C$_1$-C$_4$ alkylcarbonyl, C$_1$-C$_4$ alkoxycarbonyl and phenylcarbonyl, wherein C$_1$-C$_4$ alkylcarbonyl is unsubstituted or substituted with a group —NR11R10, wherein
R11 represents hydrogen or C$_1$-C$_4$alkyl and R10 represents hydrogen, C$_1$-C$_4$alkyl, C$_1$-C$_4$alkylcarbonyl or phenylcarbonyl;

R5 represents methyl;

R6 and R9 both represent hydrogen and

R7 and R8 independently of one another represent hydrogen or methoxy;

G represents a group selected from:
—OCO$_2$(CH$_2$)$_n$-A1, —OC(=O)CH$_2$-A2, —CH$_2$OC(=O)-A2, —CH$_2$OCO$_2$-A2, —CH$_2$NHCO$_2$-A2 and —CH$_2$CO$_2$-A2, wherein A1 represents an optionally substituted group selected from C$_1$-C$_4$alkyl, C$_6$-C$_{10}$aryl, C$_5$-C$_{10}$heteroaryl, C$_3$-C$_7$cycloalkyl and C$_5$-C$_7$heterocyclyl, A2 represents an optionally substituted group selected from C$_1$-C$_4$alkyl, C$_3$-C$_7$cycloalkyl, C$_5$-C$_7$heterocyclyl, —(CH$_2$)$_n$—C$_6$-C$_{10}$aryl and —(CH$_2$)$_n$—C$_5$-C$_{10}$heteroaryl;

n represents 0 or 1; and optionally present substituents referred to are selected from the group consisting of halogen, hydroxyl, C$_1$-C$_3$ alkyl, trifluoromethyl, C$_1$-C$_3$ alkoxy, amino, C$_1$-C$_3$ alkylamino, C$_1$-C$_3$ dialkylamino, cyano and carboxy;

and a mitochondrial inhibitor selected from metformin, buformin and phenformin.

16. The pharmaceutical product according to claim 15, comprising one or more than one dosage unit comprising a compound of formula (I) and one or more than one dosage unit comprising a mitochondrial inhibitor selected from metformin, buformin and phenformin.

17. The pharmaceutical product according to claim 15, comprising one or more than one dosage unit, each of said dosage units comprising both, a compound of formula (I) and a mitochondrial inhibitor selected from metformin, buformin and phenformin.

18. The pharmaceutical product according to claim 15, wherein the mitochondrial inhibitor is metformin and the relative amount (weight per weight) of compound of formula (I) and metformin is between 1 to 10 and 1 to 200.

19. The pharmaceutical product according to claim 15, wherein the compound of formula (I) is a compound according to claim 1.

20. A method for the determination whether a cancerous cell is responsive to a treatment with a compound of formula (I):

(I)

with the exception of syrosingopine,
wherein:
R1, R3 and R4 independently of one another represent: hydrogen, C$_1$-C$_3$ alkyl, halogen, C$_1$-C$_3$ alkoxy, amino, C$_1$-C$_3$ alkylamino, C$_1$-C$_3$ dialkylamino, or hydroxyl;

R2 represents hydrogen, $C_1$-$C_3$ alkyl, halogen, amino, $C_1$-$C_3$ alkylamino, $C_1$-$C_3$ dialkylamino, or a group —OR2a;

R2a represents hydrogen, $C_1$-$C_3$ alkyl, formyl or an optionally substituted group selected from alkylcarbonyl, alkoxycarbonyl, arylcarbonyl and heteroarylcarbonyl;

R5 represents $C_1$-$C_4$ alkyl

R6, R7, R8 and R9 independently of one another represent:

hydrogen, $C_1$-$C_3$ alkyl, halogen, $C_1$-$C_3$ alkoxy, amino, $C_1$-$C_3$ alkylamino, $C_1$-$C_3$ dialkylamino or hydroxyl;

G represents a group selected from:

—OCO$_2$(CH$_2$)$_n$-A1, —OC(=O)CH$_2$-A2, —CH$_2$OC(=O)-A2, —CH$_2$OCO$_2$-A2, —CH$_2$NHCO$_2$-A2 and —CH$_2$CO$_2$-A2, wherein A1 represents an optionally substituted group selected from alkyl, aryl, heteroaryl, cycloalkyl and heterocyclyl, A2 represents an optionally substituted group selected from alkyl, cycloalkyl, heterocyclyl, —(CH$_2$)$_n$-aryl and —(CH$_2$)$_n$-heteroaryl and n represents 0, 1, 2 or 3, said method comprising the steps of
(a) preparation of a single cell suspension and culturing the cancerous cell in a suitable media,
(b) incubating the cancerous cell with said compound of formula (I),
(c) incubating the cancerous cell of step (b) with a positively charged fluorescent dye,
(d) measuring the excitation fluorescence intensity, and
(e) comparing the measured fluorescence intensity of step (d) with the measured fluorescence intensity of the cancerous cell incubated with the positively charged fluorescent dye alone,
and wherein a relative increase of fluorescence intensity of cancerous cells pre-incubated with said compound of formula (I) indicates that said cancerous cells respond to a treatment with said compound of formula (I).

21. The method according to claim 20, wherein the compound of formula (I) is a compound according claim 1.

22. The method for treatment of a cancer or autoimmune disease or for immunosuppressive treatment of a warm-blooded animal or a human requiring such treatment, which comprises administering to said animal or human a compound of formula (I) according to claim 1 and a mitochondrial inhibitor in combination in a quantity effective against said disease or for the immunosuppressive treatment.

23. A compound of formula (I) according to claim 1, wherein the compound of formula I is

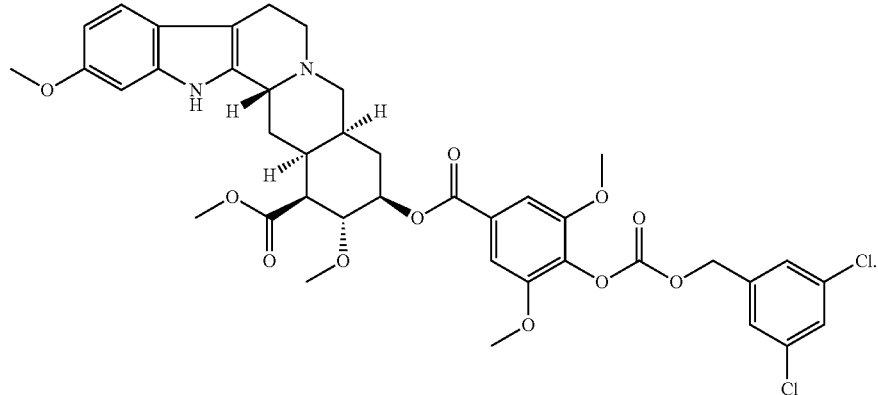 [SMILES: COC(=O)[C@H]1[C@H]2C[C@@H]3c4[nH]c5cc(OC)ccc5c4CCN3C[C@H]2C[C@@H](OC(=O)c2cc(OC)c(OC(=O)OCc3cc(Cl)cc(Cl)c3)c(OC)c2)[C@@H]1OC]

24. The pharmaceutical product according to claim 15, wherein the mitochondrial inhibitor is metformin.

25. The pharmaceutical product according to claim 15, wherein the relative amount (weight per weight) of the compound of formula (I) and mitochondrial inhibitor is between 1 to 10 and 1 to 1000.

* * * * *